(12) United States Patent
Machluf et al.

(10) Patent No.: US 9,216,236 B2
(45) Date of Patent: Dec. 22, 2015

(54) NATURAL TISSUE-DERIVED DECELLULARIZED MATRIX AND METHODS OF GENERATING AND USING SAME

(75) Inventors: Marcelle Machluf, Haifa (IL); Yuval Eitan, Haifa (IL)

(73) Assignee: Technion Research & Development Foundation Limited, Haifa (IL)

( * ) Notice: Subject to any disclaimer, the term of this patent is extended or adjusted under 35 U.S.C. 154(b) by 2332 days.

(21) Appl. No.: 11/885,640

(22) PCT Filed: Mar. 7, 2006

(86) PCT No.: PCT/IL2006/000304
§ 371 (c)(1),
(2), (4) Date: Feb. 4, 2009

(87) PCT Pub. No.: WO2006/095342
PCT Pub. Date: Sep. 14, 2006

(65) Prior Publication Data
US 2015/0050247 A1  Feb. 19, 2015

Related U.S. Application Data

(60) Provisional application No. 60/658,585, filed on Mar. 7, 2005.

(51) Int. Cl.
*A61L 27/38* (2006.01)
*A61L 27/36* (2006.01)
*C12N 5/00* (2006.01)
*A61K 35/34* (2015.01)

(52) U.S. Cl.
CPC ............ *A61L 27/3873* (2013.01); *A61K 35/34* (2013.01); *A61L 27/367* (2013.01); *A61L 27/3633* (2013.01); *A61L 27/3687* (2013.01); *A61L 27/3826* (2013.01); *C12N 5/0068* (2013.01); *A61L 2430/20* (2013.01); *C12N 2533/90* (2013.01)

(58) Field of Classification Search
None
See application file for complete search history.

(56) References Cited

U.S. PATENT DOCUMENTS

| | | | |
|---|---|---|---|
| 5,855,620 | A | 1/1999 | Bishopric et al. |
| 6,734,018 | B2 | 5/2004 | Wolfinbarger, Jr. et al. |
| 6,743,574 | B1 | 6/2004 | Wolfinbarger, Jr. et al. |
| 6,933,103 | B1 | 8/2005 | Klein et al. |
| 2002/0114845 | A1 | 8/2002 | DeVore et al. |
| 2003/0014126 | A1 | 1/2003 | Patel et al. |
| 2004/0076657 | A1 | 4/2004 | Wolfinbarger, Jr. et al. |
| 2005/0013870 | A1 | 1/2005 | Freyman et al. |
| 2005/0191281 | A1 | 9/2005 | Ollerenshaw et al. |
| 2005/0256588 | A1 | 11/2005 | Sawa et al. |

FOREIGN PATENT DOCUMENTS

| | | |
|---|---|---|
| WO | WO 96/32905 | 10/1996 |
| WO | WO 02/14480 | 2/2002 |
| WO | WO 2005/009497 | 2/2005 |
| WO | WO 2006/095342 | 9/2006 |

OTHER PUBLICATIONS

Wilson et al, Annals Thoracic Surgery, 1995, vol. 60, S353-358.*
Communication Pursuant to Article 94(3) EPC Dated Nov. 28, 2013 From the European Patent Office Re. Application No. 06711286.2.
Courtman et al. "Development of A Pericardial Acellular Matrix Biomaterial: Biochemical and Mechanical Effects of Cell Extraction", Journal of Biomedical Materials Research, XP000878572, 28(6): 655-666, Jan. 1, 1994.
Office Action Dated Feb. 24, 2011 From the Israel Patent Office Re.: Application No. 185837 and Its Translation Into English.
Office Action Dated Dec. 30, 2009 From the Israel Patent Office Re.: Application No. 185837 and Its Translation Into English.
Communication Pursuant to Article 94(3) EPC Dated Jul. 29, 2010 From the European Patent Office Re.: Application No. 06711286.2.
Badylak et al. "Extracellular Matrix for Myocardial Repair", The Heart Surgery Forum, 6(2): E20-E26, 2003.
Grauss et al. "Histological Evaluation of Decellularised Porcine Aortic Valves: Matrix Changes Due to Different Decellularisation Methods", European Journal of Cardio-Thoracic Surgery, 27(4): 566-571, 2005.
Kim et al. "Time Related Histopathologic Changes Acellularized Xenogenic Pulmonary Valved Conduits", ASAIO Journal, 50(6): 601-605, 2004.
Wilson et al. "Acellular Matrix Allograft Small Caliber Vascular Prostheses", ASAIO Transactions, American Society for Artificial Internal Organs, 36(3): M340-M343, 1990. M340, col. 2, Lines 11-14, M340, col. 2, Paragraph 2, Abstract.
Zeltinger et al. "Development and Characterization of Tissue-Engineered Aortic Valves", Tissue Engineering, 7(1): 9-22, 2001. Abstract, P.10, Paragraph 5-P.11, Paragraph 1, Fig.6.

(Continued)

*Primary Examiner* — Allison Fox

(57) ABSTRACT

Decellularized tissue-derived extracellular matrices (ECM) and methods of generating and using same are provided. The method of generating a decellularized matrix includes the steps of: (a) subjecting the tissue to washes and a hypertonic buffer; (b) subjecting the tissue to an enzymatic proteolytic digestion with an enzyme such as trypsin; and (c) removing all cellular components from the tissue using a detergent solution which includes Triton-X-100 and ammonium hydroxide. Specifically, there is provided a decellularized myocardium-derived matrix which is completely devoid of all cellular components and hence non-immunogenic in a subject, exhibits suitable structural and mechanical properties for cardiac tissue engineering or replacement therapy of damaged cardiac tissue, and is capable of remodeling upon seeding of cells.

43 Claims, 13 Drawing Sheets
(13 of 13 Drawing Sheet(s) Filed in Color)

(56) References Cited

OTHER PUBLICATIONS

International Preliminary Report on Patentability Dated Sep. 20, 2007 From the International Bureau of WIPO Re.: Application No. PCT/IL2006/000304.
Communication Pursuant to Article 94(3) EPC Dated Oct. 13, 2008 From the European Patent Office Re.: Application No. 06711286.2.
Communication Pursuant to Article 94(3) EPC Dated Mar. 22, 2012 From the European Patent Office Re.: Application No. 06711286.2.
Communication Pursuant to Article 94(3) EPC Dated May 19, 2014 From the European Patent Office Re. Application No. 06711286.2.
Response Dated Jun. 30, 2010 to Office Action of Dec. 30, 2009 From the Israel Patent Office Re.: Application No. 185837.
Response Dated Nov. 25, 2010 to Communication Pursuant to Article 94(3) EPC of Jul. 29, 2010 From the European Patent Office Re.: Application No. 06711286.2.

\* cited by examiner

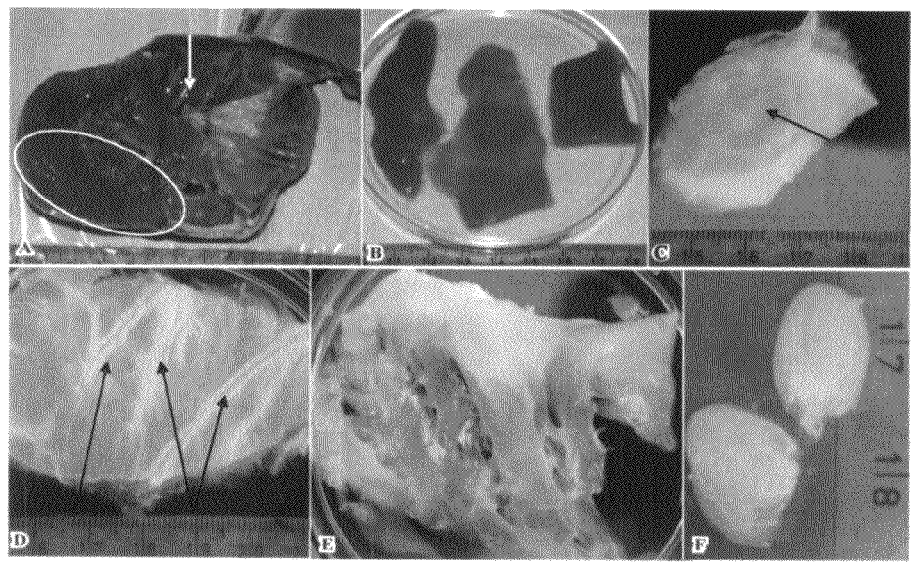
Figs. 1a-f
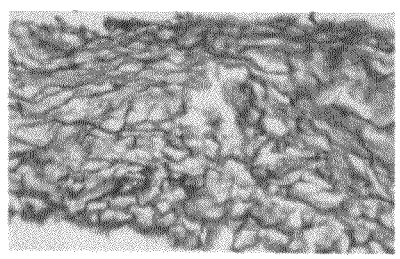
Fig. 2
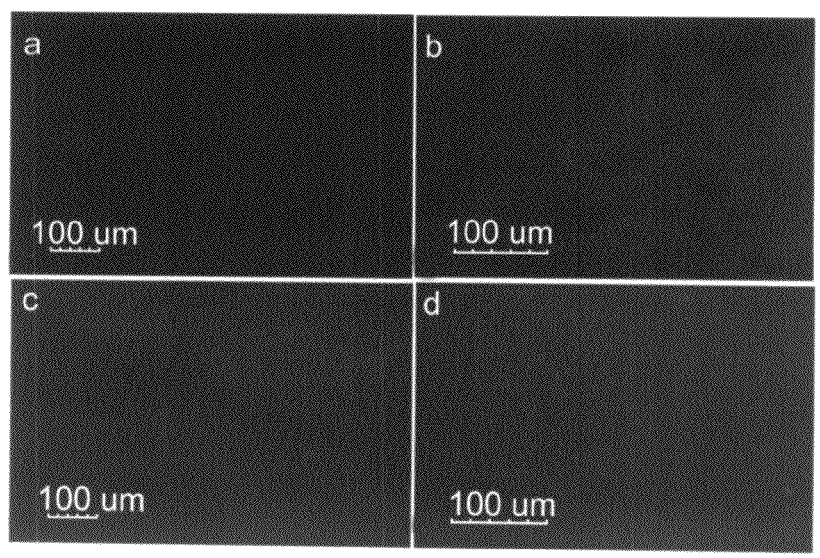
Figs. 3a-d

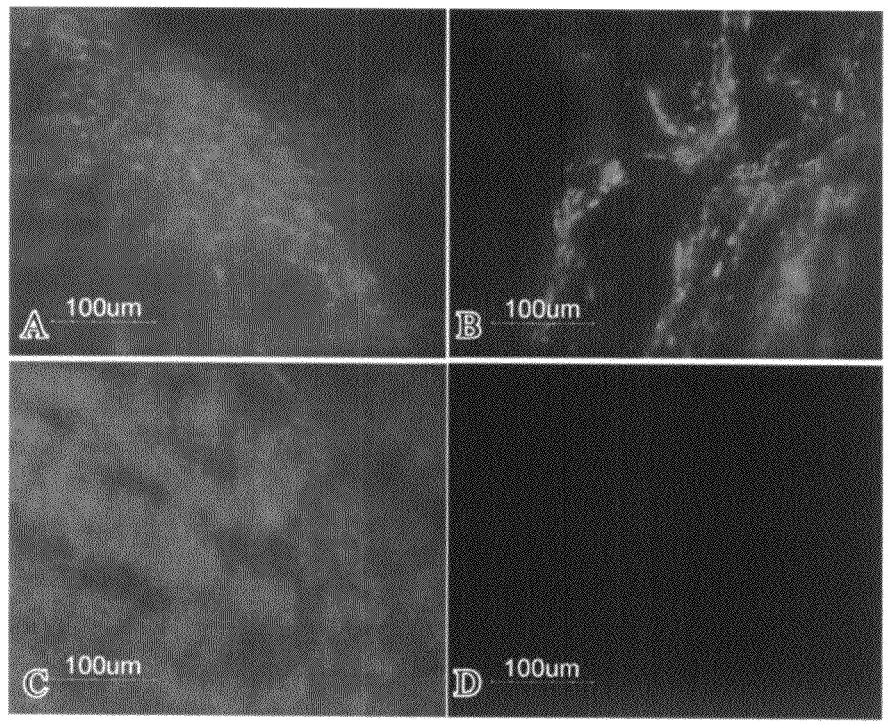
Figs. 4a-d
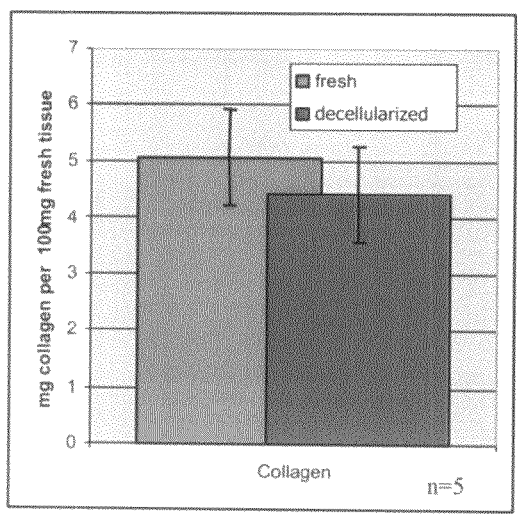
Fig. 5a
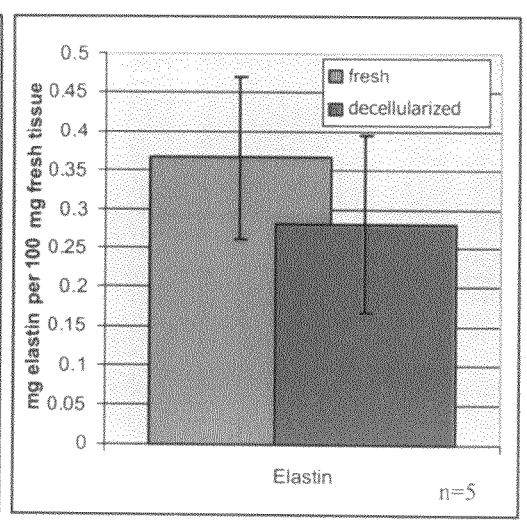
Fig. 5b

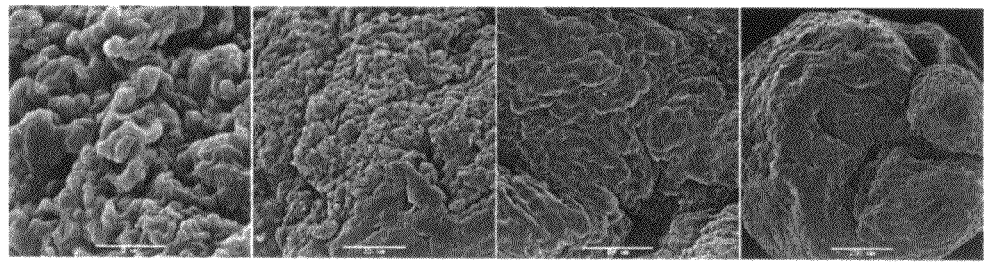
Fig. 9a    Fig. 9b    Fig. 9c    Fig. 9d
Fig. 9e    Fig. 9f    Fig. 9g
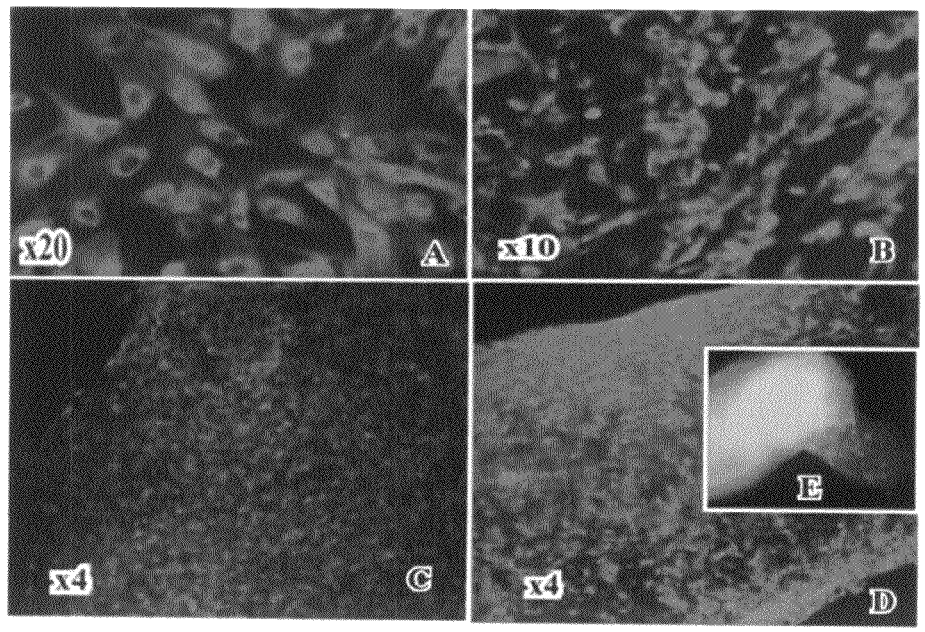
Figs. 10a-e

Figs. 11a-d

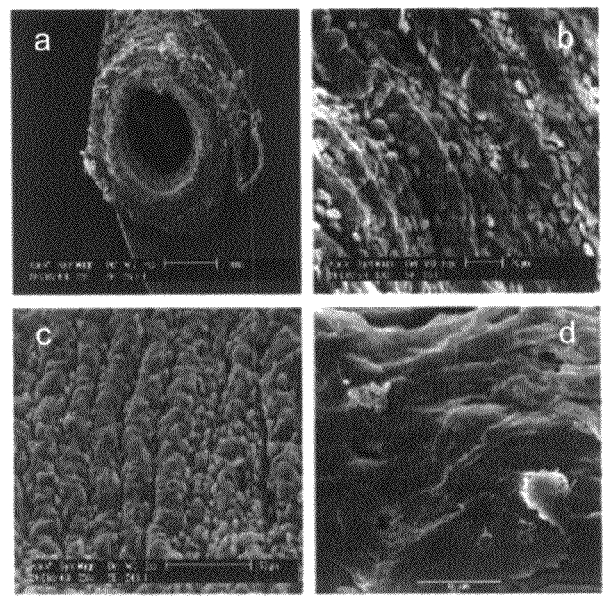
Figs. 16a-d
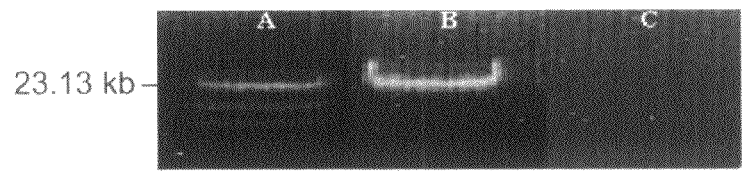
23.13 kb —
Fig. 17
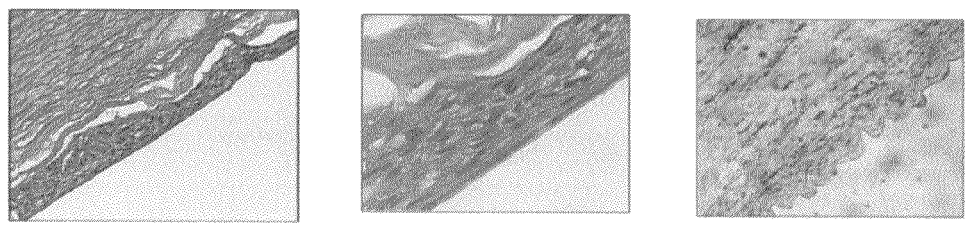
Fig. 18a　　　Fig. 18b　　　Fig. 18c

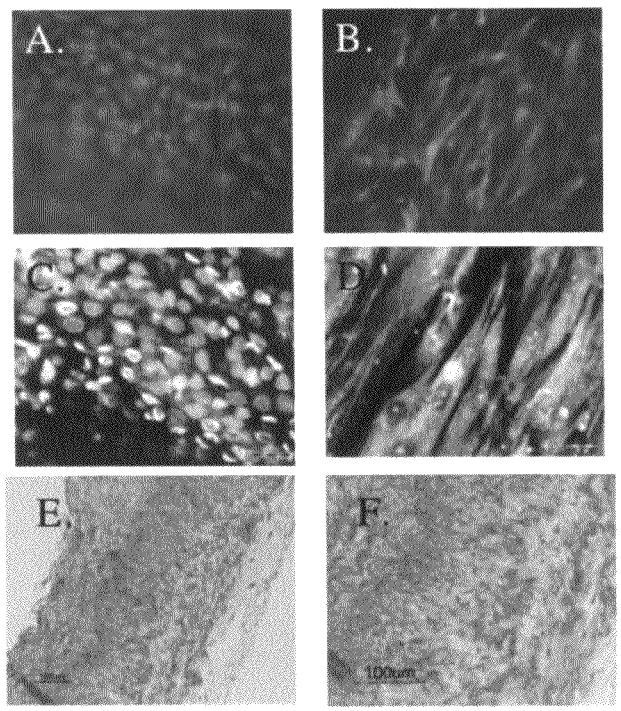
Figs. 19a-f
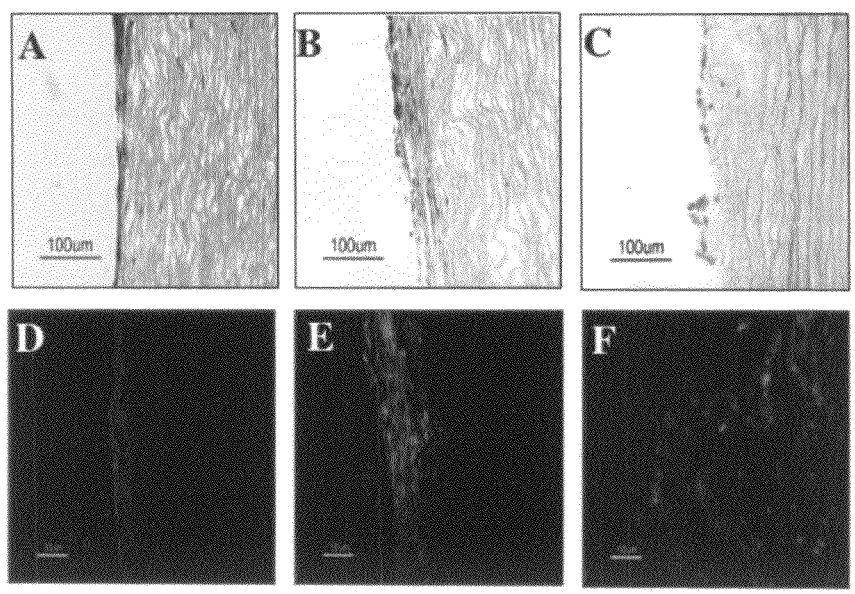
Figs. 20a-f

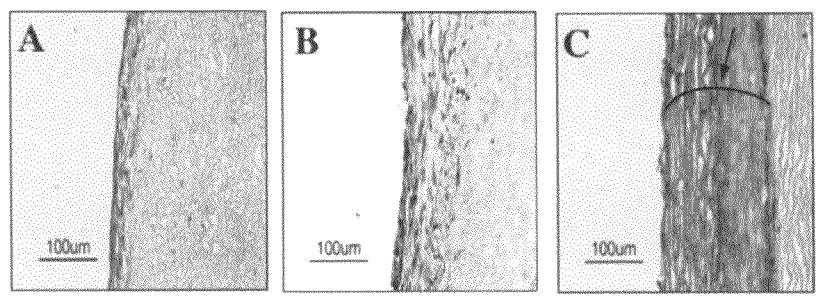
Figs. 21a-c
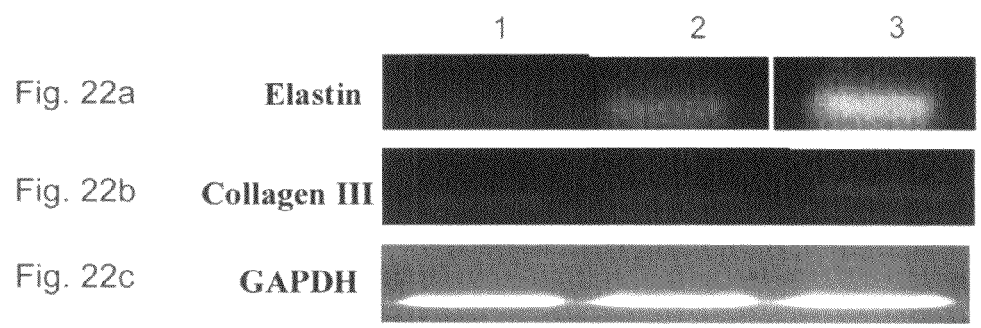
Fig. 22a Elastin
Fig. 22b Collagen III
Fig. 22c GAPDH

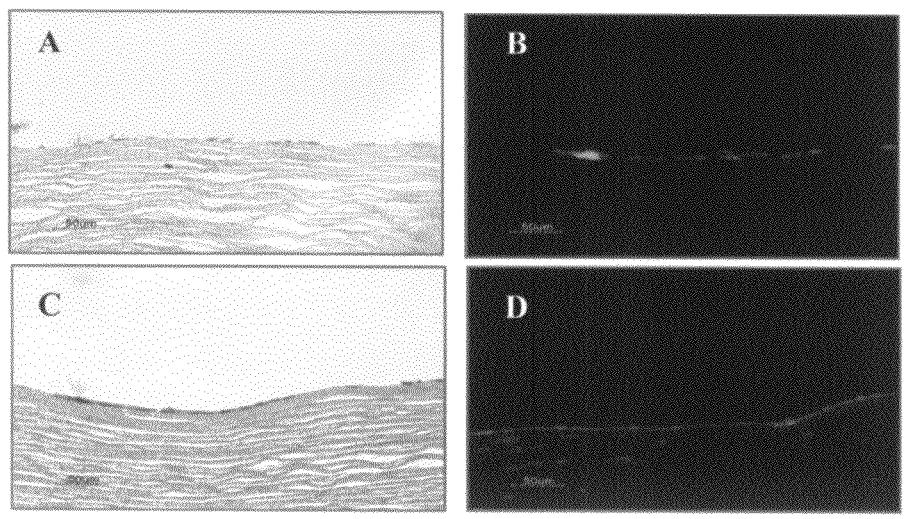
Figs. 23a-d

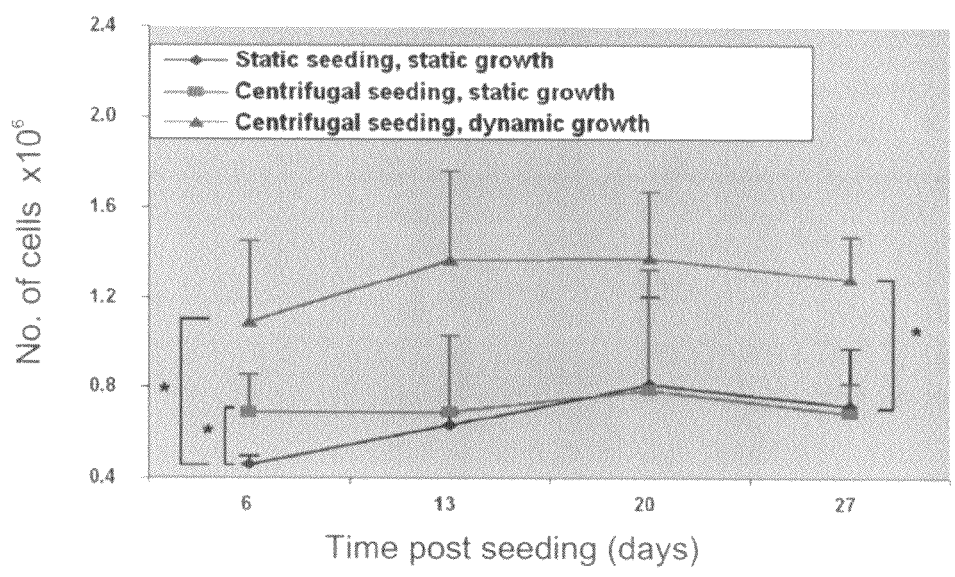
Fig. 24
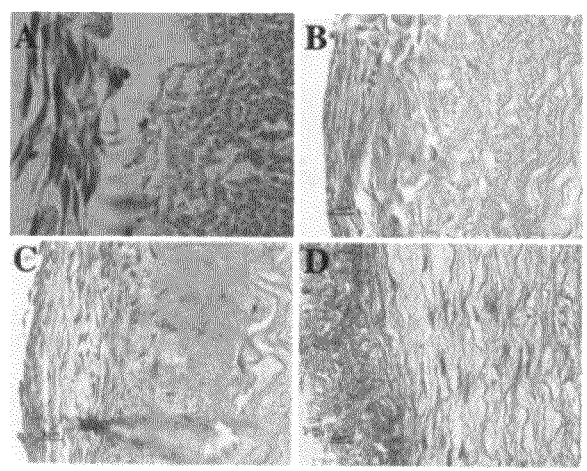
Figs. 25a-d

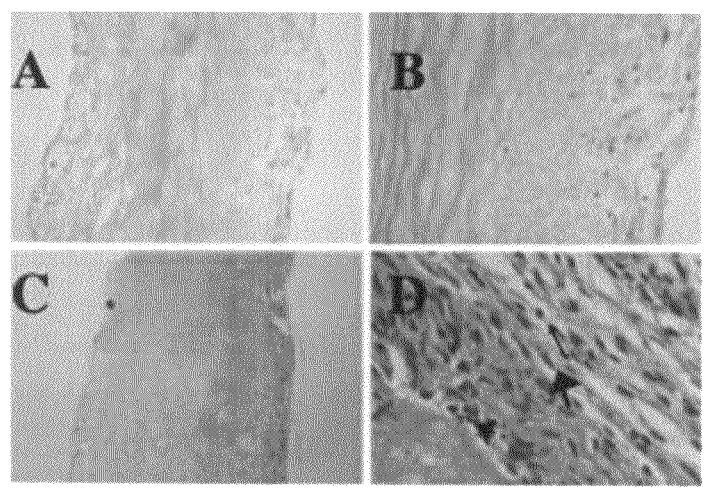
Figs. 26a-d

SEQUENCE LISTING

```
<160> NUMBER OF SEQ ID NOS: 12

<210> SEQ ID NO 1
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 1
ccttggaggt gtgtctccag                                            20

<210> SEQ ID NO 2
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 2
actttctctt ccggccacag                                            20

<210> SEQ ID NO 3
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 3
gcagggaaca acttgatggt                                            20

<210> SEQ ID NO 4
<211> LENGTH: 20
<212> TYPE: DNA
<213> ORGANISM: Artificial sequence
<220> FEATURE:
```

<223> OTHER INFORMATION: Single strand DNA oligonucleotide

<400> SEQUENCE: 4
cggatcctga gtcacagaca                                           20

<210> SEQ ID NO 5
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 5
aggtcggagt caacggattt                                           20

<210> SEQ ID NO 6
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 6
ccttctccat ggtagtgaag acc                                       23

<210> SEQ ID NO 7
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 7
gatttgctat ctcataccag gagaa                                     25

<210> SEQ ID NO 8
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 8
gacaataaag gggtcagagt aaagg                                     25

<210> SEQ ID NO 9
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 9
catggaatct gtgtcttcct aaagt                                     25

<210> SEQ ID NO 10
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 10
gttctagaga gtgctgccta atgtc                                     25

```
<210> SEQ ID NO 11
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 11
acccagaaga ctgtggatgg                                              20

<210> SEQ ID NO 12
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 12
cttgctcagt gtccttgctg                                              20
```

NATURAL TISSUE-DERIVED DECELLULARIZED MATRIX AND METHODS OF GENERATING AND USING SAME

RELATED APPLICATIONS

This Application is a National Phase of PCT Patent Application No. PCT/IL2006/000304 having International Filing Date of Mar. 7, 2006, which claims the benefit of U.S. Provisional Patent Application No. 60/658,585 filed on Mar. 7, 2005. The contents of the above Applications are all incorporated herein by reference.

FIELD AND BACKGROUND OF THE INVENTION

The present invention relates to a method of generating a decellularized extracellular matrix (ECM) from a natural tissue such that the decellularized matrix is devoid of cellular components and hence non-immunogenic when implanted in a subject, preserves the mechanical properties of the original tissue ECM and upon seeding with cells is capable of tissue remodeling. Specifically, the present invention relates to a myocardium-derived decellularized matrix suitable for myocardial tissue regeneration.

Cardiovascular disease (CVD), and particularly, coronary artery disease (CAD) such as atherosclerosis, is the main cause of death among women and men in the Western World. Atherosclerosis is a process that leads to a group of diseases characterized by a thickening of artery walls and narrowing of the internal space of coronary arteries. It accounts for nearly 75% of all deaths from CVD. Treatment options for patients with CAD include drugs, percutaneous transluminal coronary angioplasty or coronary artery bypass grafting (CABG). Bypass grafting is usually performed with autologous vascular conduits which replace or bypass diseased or occluded vessels. However, in cases of limited availability of suitable autologous vascular conduits, synthetic or natural-derived decellularized grafts can be used.

Heart failure is among the main contributors to morbidity and mortality in the Western world. The main reason for the morbidity and mortality associated with heart failure is the inability of cardiomyocytes to proliferate and regenerate following injuries such as caused by myocardial infarction (MI). Thus, the only efficient remedy for patients with acute loss of cardiac function or patients with congenital or acquired heart disease is heart transplantation. Since the demand for heart transplantation exceeds beyond the availability of donated hearts, there is a need to develop engineered cardiac tissues. The ideal cardiac tissue engineered graft should be functionally and morphologically similar to the native healthy heart tissue, integrate into the heart tissue, remain viable over time and improve the function of the damaged heart. Such an artificial heart graft should be contractile, electro-physiologically stable, flexible yet mechanically stable, readily vascularized in vivo and of autologous nature (i.e., non-immunogenic). However, to date, such an ideal cardiac tissue equivalent has not been reported.

Synthetic, natural or decellularized tissue grafts are designed to mimic the natural tissue extracellular matrix (ECM) which serves as a network supporting the attachment and proliferation of cells. The natural ECM includes molecules such as the collagen family (as a major macromolecule), elastic fibers, glycosoaminoglycans (GAG) and proteoglycans, and adhesive glycoproteins.

Synthetic tissue grafts used in the art include synthetic polymers such as polyglycolic acid (PGA), polylactic-plyglycolic acid co-polymer (PLGA), epsilon-caprolactone-co-L-lactide sponge reinforced with knitted poly-L-lactide fabric (PCLA), polydimethylsiloxane (PDMS), 1,3-trimethylene carbonate (TMC) and D,L-lactide (DLLA). Although such synthetic polymers offer good control over chemical and physical properties of the scaffold, such polymers might rapidly loose these properties and/or release inflammatory products in vivo upon degradation (Shachar and Cohen, 2003; Zimmermann and Eschenhagen, 2003). In addition, while synthetic polymers of vascular grafts have proved to be efficient when designed as large-diameter conduits (e.g., with an internal diameter larger than 5 mm), it has been difficult to develop narrower vascular grafts because of biological reactions at the blood-material and tissue-material interfaces.

Natural scaffold materials for cardiac tissue engineering include primarily ECM proteins, such as collagen and Matrigel® hydrogels, laminin and gelatin. The natural non-ECM alginate polysaccharide has also been studied as biomaterial for cardiac tissue engineering. Natural ECMs were shown to be superior to synthetic polymers in recruiting and repopulating cells in-vivo (Badylak et al, 2001). Indeed, natural tissue-derived ECMs were used in tissue engineering of heart valves (Steinhoff et al, 2000; Cebotari et al, 2002; Vesely I, 2005) and atrial septal occluder (Jux et al, 2003). However, to date, there is no report of a natural, decellularized ECM which is derived from a myocardium tissue.

Due to their bio-mechanical and non-immunogenic properties between different vertebrates, decellular ECM and collagen have become the biomaterials-of-choice for tissue engineering. The gel form of the commercially available type I collagen was used as a polymer scaffold for tissue engineered cardiac constructs [Rasidic et al., 2003; Zimmermann et al., 2002; Kofidis et al., 2002]. Prior attempts to generate decellularized ECM from natural tissues involved subjecting the tissues to enzymatic cellular digestion (e.g., using trypsin), hypotonic, hypertonic and/or low ionic strength buffers, detergent and chemical digestion (e.g., using SDS, Triton-X-100, ammonium hydroxide, peracetic acid) and non-micellar amphipatic molecules such as polyethylene glycole (PEG) (See for example, U.S. Pat. Appl. Nos. 20040076657, 20030014126, 20020114845, 20050191281, 20050256588 and U.S. Pat. Nos. 6,933,103, 6,743,574, 6,734,018 and 5,855,620; which are fully incorporated herein by reference). However, to date, there is no report of natural tissue—derived decellularized ECM which is completely devoid of cellular components and thus non-immunogenic in a subject, preserves the unique mechanical properties of the original tissue ECM prior to decellularization and which upon seeding with cells is subject to biological remodeling.

There is thus a widely recognized need for, and it would be highly advantageous to have, a method of decellularizing natural tissues devoid of the above limitations.

SUMMARY OF THE INVENTION

According to one aspect of the present invention there is provided a method of generating a decellularized extracellular matrix (ECM) of a tissue, comprising: (a) subjecting the tissue to a hypertonic buffer to thereby obtain increased intercellular space within the tissue; (b) subjecting the tissue resultant of step (a) to an enzymatic proteolytic digestion to thereby obtain digested cellular components within the tissue; and subsequently (c) removing the digested cellular components from the tissue; thereby generating the decellularized ECM of the tissue.

According to another aspect of the present invention there is provided a scaffold formed by the method.

According to yet another aspect of the present invention there is provided a scaffold comprising a myocardium-derived decellularized ECM which is completely devoid of cellular components.

According to still another aspect of the present invention there is provided an engineered tissue comprising the scaffold and a population of at least one cell type seeded and proliferated therein.

According to yet an additional aspect of the present invention there is provided a method of ex vivo forming a tissue, the method comprising: (a) seeding the scaffold with at least one type of cells; and (b) providing the cells with growth conditions so as to allow the cells to populate in the scaffold; thereby ex vivo forming the tissue.

According to still an additional aspect of the present invention there is provided a method of ex vivo forming a myocardial tissue, the method comprising: (a) seeding the scaffold with at least one type of cells; and (b) providing the cells with growth conditions so as to allow the cells to populate in the scaffold; thereby ex vivo the forming the myocardial tissue.

According to a further aspect of the present invention there is provided a method of in vivo forming of a tissue, the method comprising implanting the scaffold in a subject thereby in vivo forming the tissue.

According to yet a further aspect of the present invention there is provided a method of in vivo forming a myocardial tissue, the method comprising implanting the scaffold in a subject thereby in vivo forming the myocardial tissue.

According to further features in preferred embodiments of the invention described below, the method further comprising: (d) subjecting the tissue resultant of step (a) to a nuclease treatment to thereby obtain nucleic acid—free tissue.

According to still further features in the described preferred embodiments step (d) is effected following or concomitant with step (b).

According to still further features in the described preferred embodiments the hypertonic buffer comprises 1-1.2% NaCl.

According to still further features in the described preferred embodiments the hypertonic buffer comprises 1.1% (w/v) NaCl.

According to still further features in the described preferred embodiments the enzymatic proteolytic digestion comprises trypsin digestion.

According to still further features in the described preferred embodiments the trypsin is provided at a concentration selected from the range of 0.05-0.25% (w/v).

According to still further features in the described preferred embodiments the trypsin is provided at a concentration of 0.05% (w/v).

According to still further features in the described preferred embodiments the enzymatic proteolytic digestion is effected for about 24 hours.

According to still further features in the described preferred embodiments step (b) is effected at least twice.

According to still further features in the described preferred embodiments removing comprises subjecting the tissue to a detergent solution.

According to still further features in the described preferred embodiments the detergent solution comprises TRITON-X-100.

According to still further features in the described preferred embodiments the detergent solution further comprises ammonium hydroxide.

According to still further features in the described preferred embodiments the Triton-X-100 is provided at a concentration selected from the range of 0.1-2% (v/v).

According to still further features in the described preferred embodiments the Triton-X-100 is provided at a concentration of 1% (v/v).

According to still further features in the described preferred embodiments the ammonium hydroxide is provided at a concentration selected from the range of 0.05-1.0% (v/v).

According to still further features in the described preferred embodiments the ammonium hydroxide is provided at a concentration of 0.1% (v/v).

According to still further features in the described preferred embodiments subjecting the tissue to the detergent solution is effected for at least 24-48 hours.

According to still further features in the described preferred embodiments subjecting the tissue to the detergent solution is effected for 2-4 times.

According to still further features in the described preferred embodiments the tissue comprises a myocardium tissue.

According to still further features in the described preferred embodiments the tissue comprises a vascular tissue.

According to still further features in the described preferred embodiments the tissue comprises tissue segments.

According to still further features in the described preferred embodiments each of the tissue segments is 2-4 mm thick.

According to still further features in the described preferred embodiments the cellular components comprise cell nuclei, nucleic acids, residual nucleic acids, cell membranes and/or residual cell membranes.

According to still further features in the described preferred embodiments the myocardium-derived decellularized ECM maintains mechanical and structural properties of a myocardium tissue ECM According to still further features in the described preferred embodiments the myocardium-derived decellularized ECM is capable of remodeling upon seeding with cells.

According to still further features in the described preferred embodiments the myocardium-derived decellularized ECM maintains at least 90% of a collagen content and at least 80% of an elastin content of a myocardium tissue.

According to still further features in the described preferred embodiments the myocardium-derived decellularized ECM is characterized by a stress value of at least 0.4 MPa when strained to 40%.

According to still further features in the described preferred embodiments the myocardium tissue is a pig myocardium tissue.

According to still further features in the described preferred embodiments the at least one cell type is cardiomyocyte and the myocardium-derived decellularized ECM exhibits spontaneous beating.

According to still further features in the described preferred embodiments the spontaneous beating is in concert.

According to still further features in the described preferred embodiments the at least one type of cells comprises cardiomyocytes.

According to still further features in the described preferred embodiments the at least one type of cells comprises cardiac fibroblasts.

The present invention successfully addresses the shortcomings of the presently known configurations by providing a novel method of decellularizing natural tissues which results in matrices which are completely devoid of cellular components and thus non-immunogenic when implanted in a subject, maintain the structural and mechanical properties of the natural tissue ECMs and are remodeled when seeded with cells.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The file of this patent contains at least one drawing executed in color photograph. Copies of this patent with color photograph(s) will be provided by the Patent and Trademark Office upon request and payment of necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

Figures 6A, 6B, 6C:
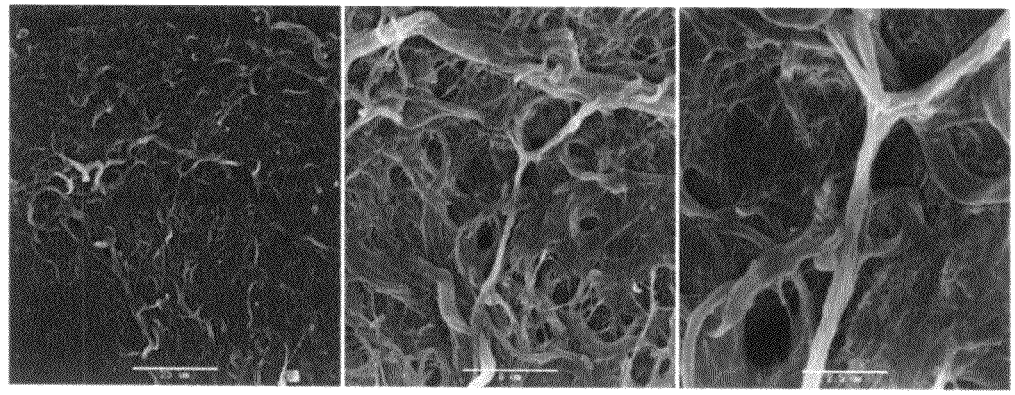

FIGS. 1 a-f are photographs depicting myocardium tissue segments from pig (FIGS. 1a-e) or rat (FIG. 1θ hearts subjected to the decellularization process of the present invention. FIG. 1a—The heart of an adult pig. The left ventricle wall is marked by a circle and the right atrium is marked by an arrow; FIG. 1b—myocardium segments of 2-4 mm thick sliced from left ventricle; FIG. 1c—myocardium segments after partial decellularization. Myocardium segments were subjected to 12 hours of proteolytic digestion in 0.05% trypsin and two cycles of incubation in a detergent solution (1% Triton-X-100/0.1% ammonium hydroxide), 48 hours each. Cellular remnants are visible in the center of the segment (marked by an arrow); FIG. 1d—myocardium segments from the left ventricle after complete decellularization as described in Example 1 of the Examples section which follows. Preservation of vascular structures is demonstrated (marked by arrows); FIG. 1e—myocardium segments from right atrium after complete decellularization. Note that the three-dimensional (3D) structure of the inner wall is preserved; FIG. 1f—The heart of an adult rat after the complete decellularization process.

FIG. 2 is a photomicrograph depicting Hematoxylin and Eosin (H&E) staining of a matrix after decellularization. Matrices after decellularization were frozen with OCT medium and 5 μm frozen sections were stained with H&E. Note that no cell nuclei are present in the matrix. Magnification is ×40.

FIGS. 3a-d are photomicrographs depicting the assessment of nuclear and nucleic acid removal using fluorescent DAPI staining. Matrices after a complete [2 cycles in 0.05% trypsin (24 hours each) and 4 cycles in a detergent solution (1% Triton-X-100/0.1% ammonium hydroxide; 48 hours each); FIGS. 3a and b;] or a partial [12 hours digestion in 0.05% trypsin and two cycles of 48 hours each in a detergent solution (1% Triton-X-100/0.1% ammonium hydroxide); FIGS. 3c and d)] decellularization process were washed in PBS and incubated for 20 minutes with 1 μg/ml DAPI. Samples were exposed to UV and examined by a fluorescent microscope. Note the absence of cell nuclei in the completely processed matrices (FIGS. 3a-b), whereas some could be found in the partially processed ones (FIGS. 3c-d). Also note that while in the partially processed matrices some residual non-nuclear staining is seen (FIGS. 3c-d) indicating incomplete removal of cellular DNA from broken nuclei, in the completely processed matrices no residual staining is seen (FIGS. 3a-b). All samples were similarly exposed to UV light for photography.

FIGS. 4a-d are photomicrographs depicting assessment of cell membrane removal using fluorescent DiO staining. Matrices following partial [12 hours digestion in 0.05 trypsin and two cycles of 48 hours each in a detergent solution (1% Triton-X-100/0.1% ammonium hydroxide); FIGS. 4a and b] or complete [two cycles of 24 hours each in 0.05% trypsin and four cycles of 48 hours each in a detergent solution (1% Triton-X-100/0.1% ammonium hydroxide); FIGS. 4c and d] decellularization process were washed in PBS and incubated in the dark at room temperature for two hours with 5 μg/ml DiO stain. Samples were inspected by a fluorescent microscope with a blue filter. FIGS. 4c and 4d represent the same field with (FIG. 4c) or without (FIG. 4d) the additional exposure to a white light. All size bars represent 100 μm. Note the presence of membrane residues in the partially processed matrices (FIGS. 4a-b) and the complete absence of membrane residues in the completely processed decellularized matrices (FIGS. 4c-d). All samples were similarly exposed to fluorescence for photography.

FIGS. 5a-b are bar graphs depicting preservation of collagen (FIG. 5a) and elastin (FIG. 5b) after complete decellularization of myocardial tissue segments. Complete decellularization was performed according to the decellularization protocol described in Example 1 of the Examples section which follows and included two cycles of 24 hours each in 0.05% trypsin and four cycles of 48 hours each in 1% Triton-X-100/0.1% ammonium hydroxide. Fresh myocardial tissue segments (fresh) and myocardium-derived decellularized ECM matrices (decellularized) were lyophilized and the total collagen and elastin contents were measured. Results are presented as the average (±SD) amount of collagen or elastin [in milligrams (mg)] per 100 mg of original fresh tissue (dry weight, n=5 in each case). Note that about 90% of the collagen and about 80% of the elastin were preserved in the matrices following complete decellularization.

FIGS. 6a-c are photomicrographs depicting SEM analysis of myocardium-derived decellularized matrices. Matrices were fixed in 2.5% glutaraldehyde, dehydrated in ascending concentrations of ethanol and subjected to SEM analysis. Note the highly fibrous and porous matrix with various thicknesses of collagen fibers and high crosslinking levels. Size bars represent 25 μm (FIG. 6a), 8 μm (FIG. 6b) and 2.5 μm (FIG. 6c).

Figure 7:
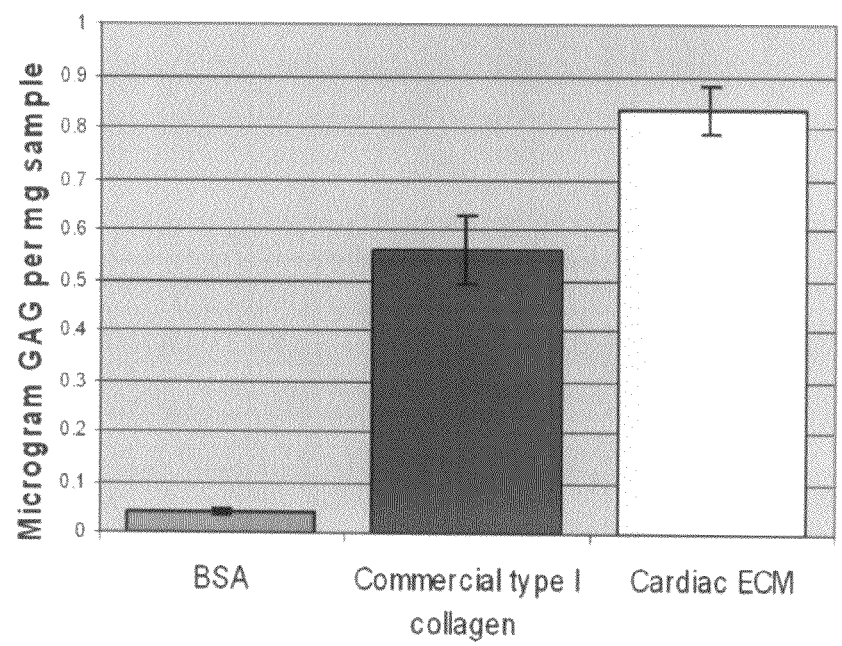

FIG. 7 is a bar graph depicting the glycosaminoglycan (GAG) content in the myocardium-derived decellularized matrix of the present invention. GAG content was quantified from lyophilized samples of the decellularized matrix of the present invention and a commercial bovine tendon type I collagen (Sigma) using the safranin O assay by extrapolation from a chondroitin sulfate standard curve. Bovine serum albumin (BSA) served as a negative control. Results are presented as average±SD of microgram GAG per mg sample as determined in six samples in each case. Note the significantly high GAG content in the myocardium-derived decellularized matrix of the present invention as compared to the commercial collagen type I matrix.

Figure 8A:
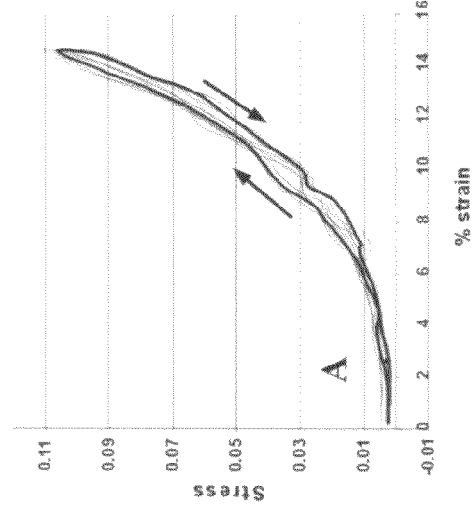
Figure 8B:
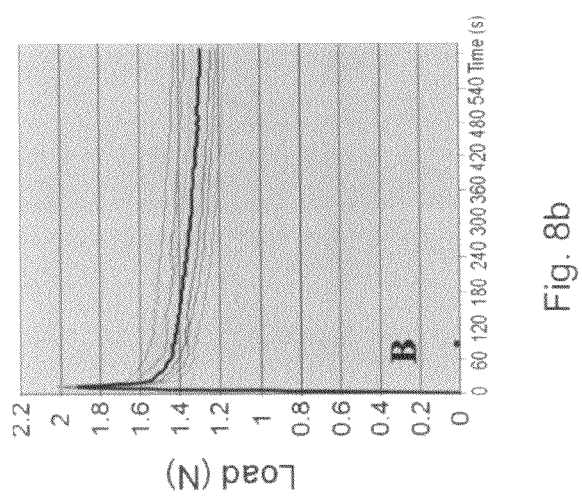
Figure 8C:
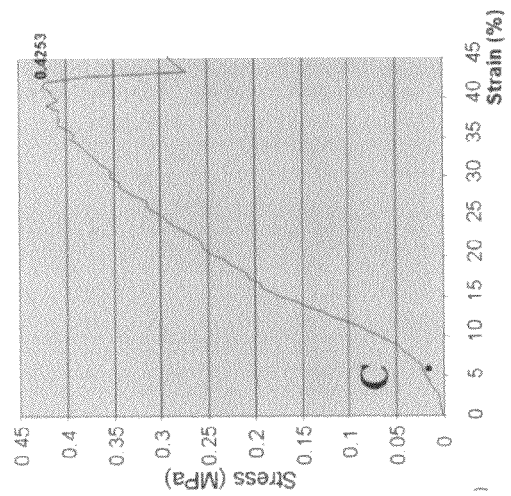

FIGS. 8a-c are graphs depicting mechanical properties of the myocardium-derived decellularized matrices of the present invention. Matrices were decellularized according to the protocol described in Example 1 of the Examples section that included two cycles of 24 hours each in 0.05 trypsin and four cycles of 48 hours each in 1% Triton-X-100/0.1% ammonium hydroxide. FIG. 8a—Cyclic strain. Matrices were pulled from "rest point" (0 stress, 0 strain) at a constant strain rate of 0.05 mm per second to 15% strain and released to the rest point at the same rate. Results are presented as the stress [in mega Pasqual (MPa) units] as a function of the percentage of strain as measured for six decellularized matrix samples. Each colored curve represents an average (of six samples) of a separate strain-release cycle [(straining to 15% strain (arrow pointing up) and releasing back to rest point (arrow pointing down)] and the bold black line represents an average of all samples in all 6 cycles. No significant decrease in elasticity is observed as indicated by retaining maximal stress during the 6 cycles of straining to 15%. FIG. 8b—Strain—relaxation. Matrices were quickly pulled (0.5 mm per second) to 20% strain and kept there for 10 minutes. Results presented as the load (in Newton [N] units) as a function of time [in seconds (s)] as measured for 6 decellularized matrices (each represented by a colored curve, bold black line indicating average of the six samples). No significant decrease in elasticity is observed as indicated by minimal decrease in load over time. FIG. 8c—Strain to break. Matrices were slowly pulled (strain rate of 0.05 mm per second) until torn. The experiment was performed on 6 decellularized matrices. Shown is a representative graph of the stress (in MPa units) as a function of percentage of strain for one decellularized matrix. Note the high strength and flexibility as indicated by withstanding a stress of up to 0.42 MPa when pulled to 40% strain.

FIGS. 9a-g are SEM (FIGS. 9a-d) and QuantomiX™ WET-SEM™ (FIGS. 9e-g) analyses of cardiac fibroblasts seeded on the myocardium-derived decellularized matrices of the present invention. Adult sheep cardiac fibroblasts were seeded at a concentration of approximately $10^4$ cells per 1 cm$^2$ matrix and following 28 days of static culturing the matrices were subjected to SEM or WET-SEM analyses. Size bars represent the following: FIG. 9a—8 µm; FIG. 9b—25 µm; FIG. 9c—80 µm; FIG. 9d—250 µm; FIG. 9e—10 µm; FIG. 9f—20 µm; FIG. 9g—500 µm. Note the significant cell density following 28 days in culture (FIGS. 9a-d) and the remodeling of the matrix by the fibroblasts into about 1 mm$^3$ spheroids (FIGS. 9d and f). Also note the new collagen fibers surrounding the cells populating the scaffold (indicated by arrows in FIG. 9e).

FIGS. 10a-e are fluorescent photomicrographs depicting cardiac fibroblast cells cultured on the decellularized matrices of the present invention. Cardiac fibroblasts were stained with the DiO stain, following which the fibroblasts were seeded on the decellularized matrices. Shown are the stained cells on the decellularized matrices at various time points after seeding: FIG. 10a—10 hours (Magnification×20); FIG. 10b—4 days (Magnification×10); FIG. 10c—12 days (Magnification×4); FIG. 10d—18 days (Magnification×4; FIG. 10e—24 days (Magnification×4). Note that three weeks after seeding the matrices began to shrink and formed dense cell populated spheres (FIGS. 10d and e).

Figure 12A:
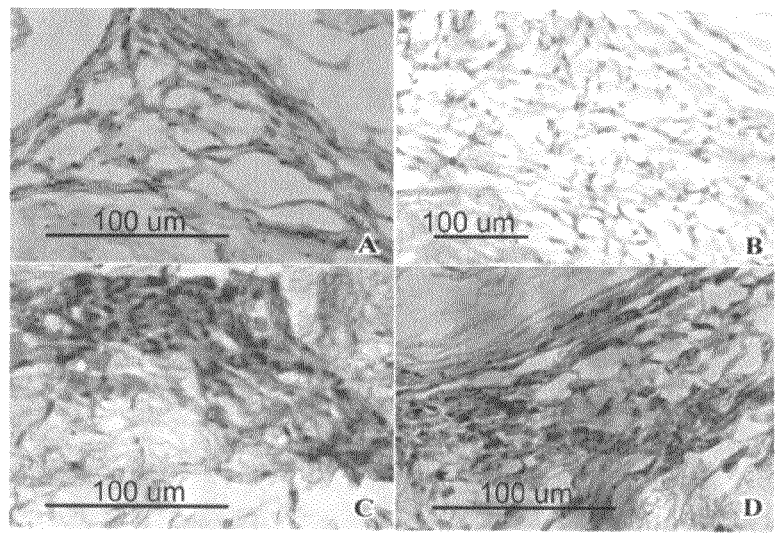
Figure 12B:
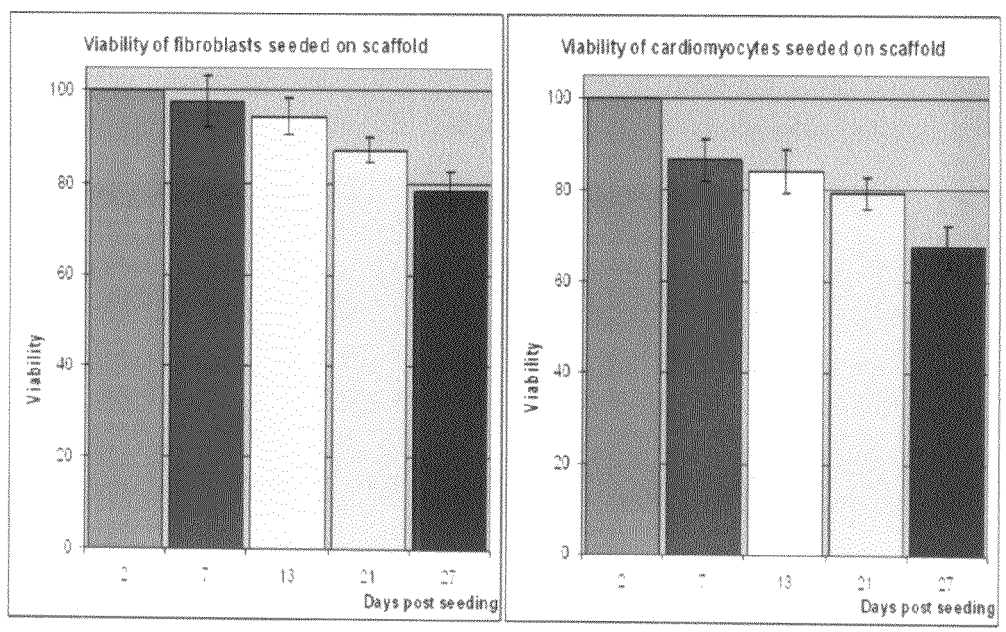

FIGS. 11a-d are photomicrographs depicting histochemical H&E staining of seeded matrices. Decellularized myocardium-derived matrices were seeded with cardiac fibroblasts and 14 (FIGS. 11a-b) or 21 (FIGS. 11c-d) days post seeding the matrices were either fixed in paraformaldehyde and embedded in paraffin blocks (FIGS. 11a and c) or frozen in OCT block (FIGS. 11b and d) and sections of 5 µm were prepared and stained with H&E. Note that 14 days post seeding the cells were distributed throughout the scaffold (FIGS. 11a-b) and that 21 days post seeding the scaffolds shrunk and the cells were populated more densely (FIGS. 11c-d). FIGS. 12a-b are bar graphs depicting the viability (in percentages) of fibroblasts (FIG. 12a) or cardiomyocytes (FIG. 12b) after seeding on the decellularized matrices of the present invention. Cells were statically seeded at a concentration of $10^4$ cells per 1-cm$^2$ scaffolds (decellularized matrices). Every second change of medium (e.g. every 4-6 days) the cells were transferred to new wells and alamarBlue was added to the medium (1/15 v/v). After 3 hours of incubation with alamarBlue, samples of 100 µl from each well were taken for fluorescent reading at 535 nm/590 nm. Values were normalized according to a standard curve of fluorescence per cell (not shown). Results are presented as the viability (in percentages, relative to the initial viability measured for each sample) as a function of days post-seeding.

Figure 13A:
Figure 13B:
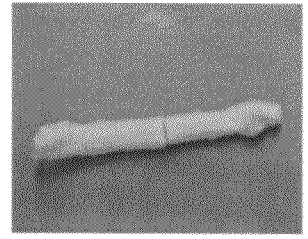

FIGS. 13a-b are photographs of a native (FIG. 13a) and a lyophilized, decellularized—porcine blood vessel (FIG. 13b). Note the clean, vasculature-free vessel obtained following the decellularization process described in Example 4 of the Examples section which follows.

Figure 14A:
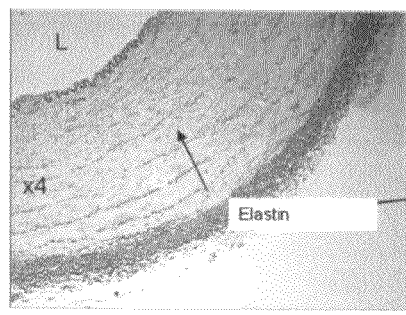
Figure 14B:
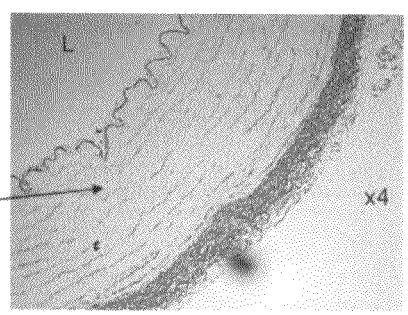

FIGS. 14a-b are photomicrographs of H&E staining depicting a natural (FIG. 14a) and a decellularized (FIG. 14b) artery. Arrows mark the elastin fibers. Note that the decellularized artery preserves the collagen and elastin structure of the natural artery tissue. Magnification is ×4.

Figure 15:
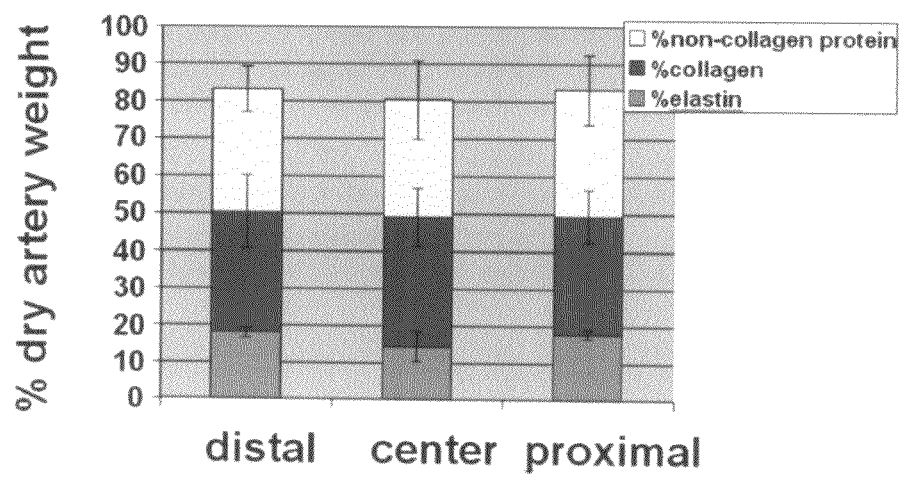

FIG. 15 is a bar graph depicting the collagen and elastin contents in the distal, center and proximal areas of decellularized arteries as percentages of dry artery weight.

FIGS. 16a-d are SEM images of native (FIGS. 16a-c) and decellularized (FIG. 16d) arteries. FIG. 16a-Image of an artery at low magnification (size bar=1 mm); FIG. 16b-Higher magnification of the outer surface of the artery shown in FIG. 16a demonstrating layers of cells (size bar=20 µm); FIG. 16c—Higher magnification of the inner surface of the artery shown in FIG. 16a demonstrating a monolayer of cells (size bar=50 µm); FIG. 16d—Image of a decellularized artery, demonstrating the complete absence of cells following the decellularization process (size bar=8 µm).

FIG. 17 is an image of an agarose gel electrophoresis of DNA samples extracted from native (lane b) or decellularized (lane c) arteries. Lane a—molecular weight size marker in kilo base pair (kb). Note that while the native artery exhibits an intense DNA band (lane b), no DNA is seen in the decellularized matrix [including absence of low molecular weight DNA in the decellularized matrix (not shown)].

FIGS. 18a-c are photomicrographs of H&E staining (FIGS. 18a-b) or α-actin immunohistochemistry (FIG. 18c; actin in dark purple) of a collagen decellularized artery scaffold seeded with smooth muscle cells. Magnification is ×10 in FIGS. 18a and c and ×40 in FIG. 18b.

FIGS. 19a-f are photomicrographs depicting recellularized porcine carotid artery (PCA) with cells expressing red fluorescent protein (RFP) or green fluorescent protein (GFP). FIG. 19a—Expression of RFP by endothelial cells four weeks after seeding (Magnification×40); FIG. 19b-Smooth muscle cells (SMC) expressing GFP four weeks post seeding (Magnification×40); FIG. 19c-Wet SEM image of FIG. 19a (Size bar=20 µm); FIG. 19d-Wet SEM image of FIG. 19b (Size bar=20 µm); FIG. 19e-f—Masson stained SMC seeded scaffold following 3 months in culture (Size bar=100 µm).

FIGS. 20a-f are photomicrographs of H&E staining (FIGS. 20a-c) or SMC actin immunostaining (FIGS. 20d-f) of decellularized artery scaffolds following 4 weeks of seeding and culturing with SMCs. FIGS. 20a and d-Static seeding and culture; FIGS. 20b and e—Centrifugal seeding and static culture; FIGS. 20c and f—Centrifugal seeding and dynamic culture. H&E stains the cell nuclei in purple and the extracellular space in pink. Actin immunostaining stains the actin protein in green and the cell nuclei in blue. Note that in the scaffold seeded by centrifugal seeding (FIGS. 20b and e) the cell penetration through the scaffold is more efficient than in the scaffold seeded by static seeding (FIGS. 20a and d). Also note that in scaffold seeded by the centrifugal seeding and cultured using dynamic culturing (FIGS. 20 c and f) cell penetration is significantly more efficient than in scaffolds seeded by centrifugal seeding and cultured by static culturing (FIGS. 20b and e). Size bars represent 100 µm in FIGS. 20a-c and 50 µm in FIGS. 20d-f.

FIGS. 21a-c are photomicrographs depicting procollagen I immunostaining of decellularized artery scaffolds following 4 weeks of seeding and culturing with SMCs. FIG. 21a—Static seeding and culture; FIG. 21b—Centrifugal seeding and static culture; FIG. 21c—Centrifugal seeding and dynamic culture. Cell nuclei are stained in purple and procollagen I is stained in brown. Note that vast amount of collagen secreted by cells that were seeded using a centrifugal method and cultured using a dynamic method (FIG. 21c, marked by an arrow). Size bars represent 100 µm.

FIGS. 22a-c are images depicting RT-PCR analysis of elastin (FIG. 22a), collagen III (FIG. 22b) and GAPDH (FIG. 22c) performed on mRNA samples derived from SMCs seeded on the decellularized artery scaffolds. Lane 1—static seeding and culture; lane 2—centrifugal seeding and static culture; lane 3—centrifugal seeding and dynamic culture. Note that the mRNA level of elastin is significantly higher in scaffolds seeded using the centrifugal seeding and cultured by the dynamic culture (FIG. 22a, lane 3) as compared to scaffolds seeded using the centrifugal seeding and cultured by static culture (FIG. 22b, lane 2) or scaffolds seeded and cultured using the static method (FIG. 22a, lane 1). The level of the GAPDH mRNA indicates that equal amounts of RNA were used in all assays.

FIGS. 23a-d are photomicrographs depicting H&E staining (FIGS. 23a and c) and CD31 immunostaining (FIGS. 23b and d) of coated artery-derived decellularized scaffolds seeded with HUVEC following 9 days in culture. FIGS. 23a-b—scaffolds coated with PBS; FIGS. 23c-d—scaffolds coated with corneal matrix (CM). CD31 immunostaining stains CD1 in green and cell nuclei in blue. Note that in the CM—coated scaffolds (FIG. 23d) the cells penetrate the scaffold more efficiently that in the PBS—coated scaffolds (FIG. 23b) as indicated by the deeper layers of nuclei stained in blue. Also note that in the CM—coated scaffolds (FIG. 23d) the endothelial cells form a more continuous layer than in the PBS—coated scaffolds (FIG. 23b) as indicated by the green labeling. Size bars represent 50 µm.

FIG. 24 is a graph depicting the proliferation of SMCs on artery-derived decellularized scaffolds at different time points. Cells were seeded and cultured using the indicated methods: blue—static seeding, static culturing; pink—centrifugal seeding, static culturing; green—centrifugal seeding, dynamic culturing. Proliferation was measured using Alamar-Blue reagent and results are presented as the number of cells×$10^6$ as a function of time (in days) post seeding. N=4, * p<0.05.

FIGS. 25a-d are photomicrographs depicting H&E staining (FIGS. 25a-c) or Masson's trichrome staining (FIG. 25d) of sections of artery-derived decellularized scaffolds which were subject to centrifugal seeding and dynamic culturing with SMCs. FIGS. 25a—1 day post-seeding; FIGS. 25b—3 weeks post-seeding; FIGS. 25c and d—7 weeks post-seeding. Masson's trichrome staining stains the cell nuclei in brown, the elastin and SMCs in red-purple and the collagen in blue. Size bars represent 50 µm.

FIGS. 26a-d are photomicrographs depicting the assessment of the immune response to implanted artery-derived decellularized scaffolds. Implanted scaffolds were harvested one (FIGS. 26a-b) or two (FIGS. 26c-d) weeks post implantation and tissue sections were stained with H&E. FIGS. 26a and c—low magnification of ×100; FIGS. 26b and d—high magnification of ×400. Note the depth of cell penetration and thickness of capsule at two weeks post implantation (FIGS. 26c and d). In FIG. 26d, arrow head pointing at a neutrophil cell; thick arrow pointing at a fibroblast; and the thin arrow pointing at a lymphocyte cell.

DESCRIPTION OF THE PREFERRED EMBODIMENTS

The present invention is of a method of generating completely decellularized ECMs from natural tissues such as myocardium or vascular tissues which are non-immunogenic when implanted in a subject, preserve the structural and mechanical properties of the natural tissue ECM and are remodeled upon seeding with cells. Specifically, the present invention can be used for tissue regeneration and/or repair applications such as of myocardial or vascular tissues.

The principles and operation of the method of generating the decellularized ECM according to the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Heart failure is a main contributor to morbidity and mortality in the Western world. The main reason for the morbidity and mortality associated with heart failure is the inability of cardiomyocytes to proliferate and regenerate following injuries such as caused by myocardial infarction (MI). Thus, the current treatment regimens for malfunctioning heart tissues rely on heart transplantation. However, due to the limited availability of donated hearts, there is a need to develop engineered cardiac tissues which can replace injured or diseased hearts.

One preferred approach of tissue engineering is the use of decellularized natural tissues. Prior art studies describe various methods of decellularization of natural tissues (See for example, U.S. Pat. Appl. Nos. 20040076657, 20030014126, 20020114845, 20050191281, 20050256588 and U.S. Pat. Nos. 6,933,103, 6,743,574, 6,734,018 and 5,855,620; which are fully incorporated herein by reference). However, none of the prior art methods resulted in complete decellularized matrices which are non-immunogenic when implanted in a subject, maintain the mechanical and structural properties of the tissue ECM and are remodeled upon seeding with cells. In addition, to date, there is no report of a decellularized matrix which is derived from a myocardium tissue.

While reducing the present invention to practice, the present inventors have uncovered a novel method of decellularizing a natural tissue so as to obtain a matrix which is completely devoid of cellular components and exhibits mechanical and structural properties that are suitable for tissue regeneration.

As described in the Examples section which follows, decellularization according to the teachings of the present invention of myocardium or artery tissues resulted in matrices which are completely devoid of all cellular components (FIG. 2 and Example 1; FIGS. 16a-d and Example 4), are non-immunogenic when implanted in a subject (FIGS. 26a-d, Example 4), maintain the ECM composition of the natural tissue (e.g., at least 90% of the collagen and 80% of the elastin; FIGS. 5a-b, 7 and Example 2; FIG. 15 and Example 4), exhibit mechanical [e.g., elasticity and rigidity (FIGS. 8a-c, Example 2 and Table 1, Example 4)] and structural (FIGS. 6a-c and Example 2; FIGS. 14a-b and Example 4) properties of the tissue ECM and are remodeled upon seeding with cells (FIGS. 9a-f, 10a-e, 11a-d; Example 3). In addition, when seeded with cardiomyocytes, the myocardium-derived decellularized matrices of the present invention exhibited spontaneous pulsatile beating in concert, similar to that of natural myocardium tissues (Example 3).

Thus, according to one aspect of the present invention there is provided a method of generating a decellularized extracellular matrix (ECM) of a tissue. The method is effected by (a) subjecting the tissue to a hypertonic buffer to thereby obtain increased intercellular space within the tissue; (b) subjecting the tissue resultant of step (a) to an enzymatic proteolytic digestion to thereby obtain digested cellular components within the tissue; and subsequently (c) removing the digested cellular components from the tissue; thereby generating the decellularized ECM of the tissue.

As used herein the phrase "decellularized ECM of a tissue" refers to the extracellular matrix which supports tissue organization (e.g., a natural tissue) and underwent a decellularization process (i.e., a removal of all cells from the tissue) and is thus completely devoid of any cellular components.

The phrase "completely devoid of any cellular components" as used herein refers to being more than 99% (e.g., 100%) devoid of the cellular components present in the natural (e.g., native) tissue. As used herein, the phrase "cellular components" refers to cell membrane components or intracellular components which make up the cell. Examples of cell components include cell structures (e.g., organelles) or molecules comprised in same. Examples of such include, but are not limited to, cell nuclei, nucleic acids, residual nucleic acids (e.g., fragmented nucleic acid sequences), cell membranes and/or residual cell membranes (e.g., fragmented membranes) which are present in cells of the tissue. It will be appreciated that due to the removal of all cellular components from the tissue, such a decellularized matrix cannot induce an immunological response when implanted in a subject.

The phrase "extracellular matrix (ECM)" as used herein, refers to a complex network of materials produced and secreted by the cells of the tissue into the surrounding extracellular space and/or medium and which typically together with the cells of the tissue impart the tissue its mechanical and structural properties. Generally, the ECM includes fibrous elements (particularly collagen, elastin, or reticulin), cell adhesion polypeptides (e.g., fibronectin, laminin and adhesive glycoproteins), and space-filling molecules [usually glycosaminoglycans (GAG), proteoglycans].

A tissue-of-interest (e.g., myocardium) may be an autologous or preferably a non-autologous tissue (e.g., allogeneic or even xenogeneic tissue, due to non-immunogenicity of the resultant decellularized matrix). The tissue is removed from the subject [e.g., an animal, preferably a mammal, such as a pig, monkey or chimpanzee, or alternatively, a deceased human being (shortly after death)] and preferably washed in a sterile saline solution (0.9% NaCl, pH=7.4), which can be supplemented with antibiotics such as Penicillin/Streptomycin 250 units/ml. Although whole tissues can be used, for several applications segments of tissues may be cut. Such tissue segments can be of various dimensions, depending on the original tissue used and the desired application. For example, for myocardium tissue regeneration tissue segments of 1-6 cm width, 1-6 cm length and 2-4 mm thick can be prepared (see Example 1 of the Examples section which follows). Alternatively, for vascular tissue regeneration, blood vessels with a diameter ranging from 5-10 mm can be cut to segments of 5-6 cm in length (see Example 4 of the Examples section which follows).

To remove the vasculature surrounding and feeding the tissue, the tissue is preferably washed at room temperature by agitation in large amounts (e.g., 50 ml per each gram of tissue segment) of EDTA solution (0.5-10 mM, pH-7.4). For example, as is described in Example 1 of the Examples section, myocardium tissue segments of 0.5-12 grams were washed in 50 ml/gram tissue of saline/EDTA solution for at least 4-5 times, 30 minutes each wash, until there was no evident of blood.

As mentioned hereinabove, the tissue of this aspect of the present invention is subjected to a hypertonic buffer to thereby obtain increased intercellular space within the tissue.

The hypertonic buffer used by the present invention can be any buffer or solution with a concentration of solutes that is higher than that present in the cytoplasm and/or the intercellular liquid within the tissue [e.g., a concentration of NaCl which is higher than 0.9% (w/v)]. Due to osmosis, incubation of the tissue with the hypertonic buffer results in increased intercellular space within the tissue.

Preferably, the hypertonic buffer used by the method according to this aspect of the present invention includes sodium chloride (NaCl) at a concentration which is higher than 0.9% (w/v), preferably, higher than 1% (w/v), preferably, in the range of 1-1.2% (w/v), e.g., 1.1% (w/v).

According to this aspect of the present invention, the tissue is subjected to the hypertonic buffer for a time period leading to the biological effect, i.e., cell shrinkage which leads to increased intercellular space within the tissue. For example, as is shown in Example 1 of the Examples section which follows, myocardium heart tissue segments of 2-4 mm thick were treated for 2 hours with a hypertonic buffer containing 1.1% NaCl-0.02% EDTA.

Following treatment with the hypertonic buffer, the tissue is further subjected to an enzymatic proteolytic digestion which digests all cellular components within the tissue yet preserves the ECM components (e.g., collagen and elastin) and thus results in a matrix which exhibits the mechanical and structural properties of the original tissue ECM. It will be appreciated that measures are taken to preserve the ECM components while digesting the cellular components of the tissue. These measures are further described hereinbelow and include, for example, adjusting the concentration of the active ingredient (e.g., trypsin) within the digestion solution as well as the incubation time.

Proteolytic digestion according to this aspect of the present invention can be effected using a variety of proteolytic enzymes. Non-limiting examples of suitable proteolytic enzymes include trypsin and pancreatin which are available from various sources such as from Sigma (St. Louis, Mo., USA). According to one preferred embodiment of this aspect of the present invention, proteolytic digestion is effected using trypsin.

Digestion with trypsin is preferably effected at a trypsin concentration ranging from 0.01-0.25% (w/v), more preferably, 0.02-0.2% (w/v), more preferably, 0.05-0.1 (w/v), even more preferably, a trypsin concentration of about 0.05% (w/v). For example, as is described in Example 1 of the Examples section which follows, a trypsin solution containing 0.05% trypsin (w/v; Sigma), 0.02% EDTA (w/v) and antibiotics (Penicillin/Streptomycin 250 units/ml), pH=7.2] was used to efficiently digest all cellular components of the myocardium tissue.

It will be appreciated that for efficient digestion of all cellular components of the tissue, each of the tissue segments is preferably placed in a separate vessel containing the digestion solution (e.g., a trypsin solution as described hereinabove) in a ratio of 40 ml digestion solution per each gram of tissue. Preferably, while in the digestion solution, the tissue segments are slowly agitated (e.g., at about 150 rpm) to enable complete penetration of the digestion solution to all cells of the tissue.

It should be noted that the concentration of the digestion solution and the incubation time therein depend on the type of tissue being treated and the size of tissue segments utilized and those of skilled in the art are capable of adjusting the conditions according to the desired size and type of tissue. For example, when a myocardium tissue is treated, the tissue is preferably cut to segments of 2-4 mm thick and digestion is effected by two cycles of incubation in the digestion solution, each effected for 24 hours (i.e., a total of 48 hours). Shorter incubation periods of such tissue segments can result in incomplete decellularization as is shown in FIGS. 3c-d and 4a-b and described in Example 1 of the Examples section which follows. Alternatively, when an artery tissue is treated, tissue segments of 5-6 cm in length are subjected to 2 cycles of digestion, each effected for 24 hours in the digestion solution.

Preferably, the tissue segments are incubated for at least about 20 hours, more preferably, at least about 24 hours. Preferably, the digestion solution is replaced at least once such that the overall incubation time in the digestion solution is at least 40-48 hours.

Following incubation in the digestion solution, the digested cellular components are removed from the tissue. Removal of the digested components from the tissue can be effected using various wash solutions, such as detergent solutions (e.g., ionic and non ionic detergents such as SDS Triton X-100, Tween-20, Tween-80) which can be obtained from e.g., Sigma (St. Louis, Mo., USA) or Biolab (Atarot, Israel, Merck Germany).

Preferably, the detergent solution used by the method according to this aspect of the present invention includes TRITON-X-100 (available from Merck). For efficient removal of all digested cellular components, TRITON-X-100 is provided at a concentration range of 0.05-2.5% (v/v), more preferably, at 0.05-2% (v/v), more preferably at 0.1-2% (v/v), even more preferably at a concentration of 1% (v/v).

Preferably, for optimized results, the detergent solution includes also ammonium hydroxide, which together with the TRITON-X-100, assists in breaking and dissolving cell nuclei, skeletal proteins, and membranes.

Preferably, ammonium hydroxide is provided at a concentration of 0.05-1.5% (v/v), more preferably, at a concentration of 0.05-1% (v/v), even more preferably, at a concentration of 0.1-1% (v/v) (e.g., 0.1%).

The concentrations of TRITON-X-100 and ammonium hydroxide in the detergent solution may vary, depending on the type and size of tissue being treated and those of skills in the art are capable of adjusting such concentration according to the tissue used.

Incubation of the tissue (or tissue segments) with the detergent solution can last from a few minutes to hours to even several days, depending on the type and size of tissue and the concentration of the detergent solution used and those of skills in the art are capable of adjusting such incubation periods. Preferably, incubation with the detergent solution is effected for at least 24-72 hours, and even more preferably, 2-4 cycles of incubation with the detergent solution are effected (e.g., a total of 192 hours).

The above described detergent solution is preferably removed by subjecting the matrix to several washes in water or saline (e.g., at least 10 washes of 30 minutes each, and 2-3 washes of 24 hours each), until there is no evident of detergent solution in the matrix.

Although as described hereinabove, incubation with the detergent solution enables the removal of cell nuclei, proteins and membrane, the method according to this aspect of the present invention optionally and preferably includes an additional step of removing nucleic acids (as well as residual nucleic acids) from the tissue to thereby obtain a nucleic acid—free tissue. As used herein the phrase "nucleic acid—free tissue" refers to a tissue being more than 99% free of any nucleic acid or fragments thereof as determined using conventional methods (e.g., spectrophotometry, electrophoresis essentially as described in Example 1 of the Examples section which follows). Such a step utilizes a DNase solution (and optionally also an RNase solution). Suitable nucleases include DNase and/or RNase [Sigma, Bet Haemek Israel, 20 µg/ml in Hank balance salt solution (HBSS)]. It will be appreciated that the nuclease treatment is effected following or concomitant with the proteolytic digestion described in step (b).

Thus, the teachings of the present invention can be used to generate a scaffold suitable for tissue regeneration. As used herein the terms "scaffold" or "matrix" which are interchangeably used herein, refer to a two-dimensional or a three-dimensional supporting framework. Preferably, the scaffold of the present invention can be used to support cell growth, attachment, spreading, and thus facilitate cell growth, tissue regeneration and/or tissue repair. The scaffold of the present invention can be formed from any natural tissue such as vascular tissue (e.g., artery, vein), muscle tissue (e.g., myocardium, skeletal muscle), bladder tissue, nerve tissue and testicular tissue. As is described hereinabove, the natural tissue can be derived from a subject such as an animal (e.g., pig) or a deceased human being.

Using the above teachings, the present inventors have generated, for the first time, a scaffold which comprises a myocardium-derived decellularized ECM which is devoid of cellular components and is suitable for tissue regeneration.

As used herein the phrase "suitable for tissue regeneration" refers to a scaffold, which upon seeding and culturing with cells (ex-vivo) and/or upon implantation in a subject (in-vivo) is capable of regenerating or repairing a tissue-of-interest (e.g., a myocardium tissue).

Due to the unique decellularization method of the present invention, which is based on treating the tissue with a hypertonic buffer followed by an enzymatic proteolytic digestion using for example, trypsin, and subsequently removing the digested cellular components with the detergent solution, the scaffolds the present invention are completely devoid of cellular components.

For example, as is shown in Examples 1 and 4 of the Examples section which follows, myocardium-derived or artery-derived decellularized matrices prepared according to the teachings of the present invention were devoid of cells (see FIG. 2 for myocardium-derived ECM and FIGS. 16a-d for artery-derived ECM), cell nuclei (see FIGS. 3a-b for myocardium-derived ECM), nucleic acids (see FIG. 17 for artery-derived ECM) and cell membranes (see FIGS. 4c-d for myocardium-derived ECM). Methods of assessing the acellularity (i.e., the complete absence of cellular components) of the scaffolds of the present invention are described in Example 1 of the Examples section which follows and include detection of cells, cell nuclei, nucleic acids, residual nucleic acids, membranes and residual membranes.

Preferably, scaffolds generated according to the teachings of the present invention maintain the mechanical and structural properties of the natural tissue ECM and thus are suitable for tissue regeneration and/or repair. As used herein the phrase "mechanical properties" refers to the elasticity (i.e., the tendency of the matrix to return to its original shape after it has been stretched or compressed) and strength (i.e., the resistance to tearing or breaking upon subjecting the matrix to a load or stress) of the scaffold. The phrase "structural properties" refers to the structure and shape of the matrix in terms of fiber configuration, diameter and/or composition (e.g., percentages of collagen, elastin and/or GAG). The mechanical and structural properties of the scaffold of the present invention enable the scaffold to regenerate and/or repair a damaged or diseased tissue when seeded with cells and/or implanted in a subject (e.g., a human being in need of tissue regeneration). It will be appreciated that the mechanical properties of a native or an engineered tissue are determined by the combination of mechanical and structural properties of the ECM and the cells present in the tissue. For example, in a myocardium tissue, the contraction of the myocardium tissue (i.e., beating) is a result of the combined action of the cells on the unique ECM composition and structure of the myocardium tissue.

For example, as is shown in Example 2 of the Examples section which follows, myocardium-derived decellularized matrices were elastic (e.g., flexible) yet retained their strength following repetitive slow straining (FIG. 8a) or constant quick straining to 20% (FIG. 8b). In addition, when strained to 40% along one of the axis, the myocardium-derived decellularized matrices retained a strength of 0.42 MPa before tearing (FIG. 8c).

Preferably, the myocardium-derived decellularized ECM maintains at least 90% of the collagen content and at least 80% of the elastin content of a native myocardium tissue.

According to one preferred embodiment of the present invention, scaffolds generated according to the method of decellularization of the present invention are capable of remodeling upon seeding with cells.

As used herein the phrase "capable of remodeling upon seeding with cells" refers to the ability of the matrix (or the scaffold) to change its geometrical shape and/or chemical composition as a result of cells being seeded and proliferating therein. A change in the geometrical shape can be, for example, becoming round (e.g., spheric), thick, dense, narrow and the like. A change in the chemical composition can be increased concentrations of one of the scaffold components such as elastin, collagen, GAG and the like. Such remodeling can occur following a certain period in culture or following implantation in a body. For example, as is shown in FIGS. 9a-f, 10a-e and 11a-d and is described in Example 3 of the Examples section which follows, three weeks following seeding and culturing with cardiac fibroblasts, the myocardium-derived scaffolds were remodeled, e.g., began to shrink and formed dense cell population spheres.

Thus, the scaffolds of the present invention can be seeded with cells and cultured under suitable culturing conditions to thereby form an engineered tissue. The scaffolds can be seeded with one type or several types of cells depending on the desired application.

For example, for the engineering of a vascular tissue, the scaffold can be seeded with smooth muscle cells (SMCs) and/or endothelial cells as is further described in Example 4 of the Examples section which follows.

For engineering of a myocardium tissue, the scaffold is preferably seeded with cardiomyocyte and/or cardiac fibroblast as is further described in Example 3 of the Examples section which follows Various methods can be used to seed and culture the cells within the scaffold of the present invention. These include, but are not limited to, static seeding, centrifugal seeding, static culturing and dynamic culturing (for seeding and culturing methods see Example 4 of the Examples section which follows).

It will be appreciated that a scaffold formed from a certain tissue can be used for the regeneration and/or repair of the same type of tissue or even for the regeneration and/or repair of a different type of tissue as long as both tissues share ECMs with similar composition and structure. For example, myocardium tissue for bladder wall tissue regeneration, blood vessels for bladder wall tissue regeneration, blood vessels for heart tissue (e.g., myocardium) regeneration and cardiac or blood vessels for testicular sac tissue regeneration and/or repair.

Preferably, the engineered myocardium tissue of the present invention which is seeded and cultured with cardiomyocytes exhibits spontaneous beating. As used herein the phrase "spontaneous beating" refers to an independent contraction of the matrix which results from the endogenous electrophysiological activity of the cardiomyocytes seeded on the matrix. Preferably, such spontaneous beating is obtained following 1-2 days in culture, however, it will be appreciated that spontaneous beating can also occur earlier, depending on the concentration of cells being seeded, the cardiomyocyte isolation method (e.g., the method described in Example 4) and the culturing conditions (e.g., medium used, medium supplements such as growth factors, amino acids, minerals and the like).

Preferably, the spontaneous beating of the engineered tissue is in concert. As used herein the phrase "beating in concert" refers to a well-coordinated beating which includes all cells of the tissue and wherein each cell contracts at a specific moment such that all cells of the tissue form an efficient muscle-like contraction. Such spontaneous concert pulsatile beating can be observed following 3-4 days of seeding the cells on the scaffolds and can continue, while cultured ex vivo, for at least 3 weeks (see Example 3 of the Examples section which follows).

Thus, the teachings of the present invention can be used to form a tissue ex vivo or in vivo.

As used herein, the phrase "ex vivo" refers to forming a tissue from living cells (derived from an organism) by culturing them on the scaffold of the present invention outside of the living organism (e.g., in a culture medium).

For ex vivo tissue formation the scaffold is seeded with cells and is further subjected to growth conditions (e.g., culture medium with growth factors, amino acids, serum, antibiotic and the like, incubation temperature, % of $CO_2$) which enable the cells seeded thereon to populate and thus form the tissue-of-interest (e.g., a cardiac tissue, nerve tissue, bladder wall, testicular sac, kidney and the like).

The term "seeded" refers to a scaffold which is being encapsulated, entrapped, plated, placed and/or dropped with cells. It will be appreciated that the concentration of cells which are seeded on or within the scaffold of the present invention depends on the type of cells and decellularized scaffold used.

For example, to induce the formation of an artery (e.g., for bypass a damaged artery), an artery-derived decellularized scaffold is seeded with SMCs at a concentration of 100,000-200,000 per 1 $cm^2$ using the centrifugal method (e.g., by overnight incubation in a spinner flask) followed by culturing in the spinner flask for 7 weeks, essentially as described in Example 4 of the Examples section which follows.

Tissues which are formed ex vivo can be further implanted in a subject in need thereof (e.g., a subject in need of vascular or myocardium tissue regeneration and/or repair) using techniques known in the art (e.g., using a surgical tool such as a scalpel, spoon, spatula, or other surgical device) to thereby regenerate and/or repair the tissue-of-interest.

The phrase "in vivo" refers to forming a tissue within a living organism such as a plant or an animal, preferably in mammals, preferably, in human subjects.

For in vivo tissue formation, the scaffold is implanted in a subject in need thereof and the cells of the subject populate and proliferate therein to thereby form or repair the tissue-of-interest.

As used herein the term "about" refers to ±10%.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., Ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (Eds.) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., Ed. (1994); "Culture of Animal Cells—A Manual of Basic Technique" by Freshney, Wiley-Liss, N.Y. (1994), Third Edition; "Current Protocols in Immunology" Volumes I-III Coligan J. E., Ed. (1994); Stites et al. (Eds.), "Basic and Clinical Immunology" (8th Edition), Appleton & Lange, Norwalk, Conn. (1994); Mishell and Shiigi (Eds.), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., Ed. (1984); "Nucleic Acid Hybridization" Hames, B. D., and Higgins S. J., Eds. (1985); "Transcription and Translation" Hames, B. D., and Higgins S. J., Eds. (1984); "Animal Cell Culture" Freshney, R. I., Ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Decellularization of Myocardium-Derived ECM and Assessment of the Decellularized Matrix Cellular components are the main cause for immune responses against xenografts, therefore, for tissue regeneration and/or repair, tissue-derived decellularized matrices must be devoid of all cellular components. Prior art studies have suggested that removal of cellular components can be effected by digesting the tissues with proteases such as trypsin. However, excess enzymatic digestion might ultimately result, in undesired damage to the ECM structure, strength and elasticity. Thus, to obtain a tissue-derived decellularized matrix devoid of all cellular components yet capable of exhibiting the mechanical properties desired for such tissue constructs, the present inventors have devised, after laborious experimentations, the following efficient and well-calibrated decellularization protocol.

Materials and Experimental Methods

Dissection of myocardium tissues—Hearts of adult male and female pigs were harvested in a local slaughterhouse (Iblin Village, Israel). Immediately after harvest, hearts were soaked and kept in cold sterile saline (pH=7.4) supplemented with antibiotics (Penicillin/Streptomycin 250 units/ml), until isolation process was performed in the laboratory (maximum time periods in cold sterile saline was two hours). Myocardium muscle tissue was manually dissected into slices parallel to the epicardium, with or without the epicardial membrane. Visual fatty accumulations, if any, were removed.

Preliminary washes—To remove residual blood, the myocardium tissue segments were washed at room temperature by agitation in large amounts (e.g., 50 ml per gram tissue segment) of EDTA (0.5-10 mM, pH-7.4) in saline. Solution was changed every 30 minutes, at least four or five times, until there was no evident blood. Myocardium tissue segments were then agitated for two hours in a hypertonic buffer consisting of 1.1% NaCl-0.02% EDTA. Incubation of the myocardium tissue segments in the hypertonic buffer induces an osmotic pressure which results in diffusion of water out of the cells and/or the intercellular space, resulting in increased intercellular space, thus enhancing accessibility of tissue substrates for the subsequent enzymatic digestion.

Enzymatic cell digestion—Myocardium tissue segments were subjected to one or two cycles of 24 hours each of enzymatic cell digestion in trypsin-EDTA [0.05-0.25% trypsin (w/v), 0.02-0.1% EDTA (w/v), antibiotics (Penicillin/Streptomycin 100-250 units/ml), pH=7.2]. The tissue segment were agitated at 150 revolutions per minutes (rpm) in separate sterile vessels at 37° C. Ratio of digestion solution volume to tissue weight was at least 40 ml of digestion solution per each gram of tissue.

Enzymatic nucleic acid removal—To assure nucleic acid removal, Trypsin digested matrices were subjected to digestion with 5-25 µg/ml DNase I (Roche, France) in Hank's Buffered Salt Solution (HBSS), pH=7.2, with antibiotics (Penicillin/Streptomycin 100-250 units/ml). Matrices were agitated at 150 rpm overnight at 37° C.

Detergent decellularization—Cells and cellular components were further removed from matrices with Triton® X-100 (0.1-2%; Merck) and ammonium hydroxide (0.05-1.0%, Frutarom) in an isotonic solution of 0.9% NaCl. Segments were agitated at 150 rpm for 48 hours at 4° C. in the detergent solution, following which the detergent solution was replaced with a fresh detergent solution. This step was repeated two-four more times. Decellular matrices were then subjected to several washes in sterile saline (at least 10 washes of 30 minutes each, and 2-3 washes of 24 hours each), until the complete removal of the detergent residue (as evident by no foaming of the wash solution after vigorous shaking).

Lyophilization and sterilization—Matrices were washed several times in large volumes of double-distilled sterile water to remove remaining salts. The matrices were then spread in 6-cm tissue culture plastic dishes, and excess water was removed. For lyophilization, the matrices were snap-frozen in liquid nitrogen and lyophilized for 12 hours. Dry matrices were then cut into the desired shape and size (e.g. ~11-13 mm squares or disks, suitable for placing in 24-well culture plates). Lyophilized matrices were sterilized in cold ethylene-oxide gas and ventilated for at least one week before further use. Alternatively, matrices were exposed to ultraviolet light radiation for a few hours under sterile condition, desiccated with silica gel beads to prevent re-hydration by air moisture. Alternatively, non-lyophilized matrices were soaked overnight in 70% ethanol, washed with sterile water and kept in PBS at 4° C. Under these sterilization methods shelf life of decellularized matrices was practically eternal.

This process of decellularization was optimized for complete removal of cellular components on one hand, and minimum loss of matrix collagen and desired mechanical properties on the other.

Decellularization assessment—For initial evaluation of acellularity (i.e., absence of cellular components), the decellularized matrices were fixed in 10% formalin in PBS, blocked in paraffin and 5 µm sections were subjected to standard Hematoxylin and Eosin (H&E) staining.

Presence of cell nuclei—The presence of nuclei was detected using a fluorescent staining with DAPI (4',6-diamidino-2-phenylindole, Molecular Probes, Inc., Eugene, Oreg., USA). This fluorophore incorporates into nuclear double-stranded compact DNA, regardless if cells are viable or not. Decellularized matrices were immersed for 20 minutes at room temperature in 0.5 µg/ml DAPI in PBS (pH=7), washed in PBS and inspected by a fluorescent microscope (excitation—358 nm, emission—461 nm).

Presence of cell membranes—The presence of cell membranes was detected by fluorescent staining with lipophilic DiO (3,3'-dioctadecyloxacarbocyanine perchlorate, Molecular Probes, Inc., Eugene, Oreg., USA). In aqueous solutions DiO hardly fluoresces, but becomes photo-stably and highly fluorescent when incorporates into bilayered phospholipid membranes. Decellularized matrices were immersed for 2 hours at room temperature with 5 µg/ml DiO stain in PBS (pH=7), washed in PBS and inspected by a fluorescent microscope (excitation—484 nm, emission—501 nm).

Presence of residual nucleic acids—The presence of residual nucleic acids was detected by phenol-chloroform extraction from NaOH—digested matrices. Matrices were digested over-night at 90° C. in 10 mM NaOH. DNA was extracted from the aqueous digest by the well-known phenol-chloroform method. Extracted DNA was visualized by electrophoresis on 0.8% agarose gel and quantified by photometric absorbance at 280/260 nm.

In all the above described decellularization assessment methods cells seeded on coverslips served as positive control, rat-tail type I collagen hydrogel (3.0 mg/ml) served as negative control.

Experimental Results

ECM decellularization process—The decellularization process presented here has been optimized for complete removal of cells and cellular components, while minimally compromising the ECM composition and mechanical properties. FIGS. 1a-f depict myocardium tissues undergoing the decellularization process of the present invention.

Segments of myocardium tissue (2-4 mm thick) were removed from the left ventricular wall and the right atrium (FIGS. 1a-b) of a pig heart. Following washes, incubation in a hypertonic buffer and the subsequent enzymatic digestion with trypsin, the rigid muscle tissue segments softened, however the tissue segments did not loose their solid brown color, indicating that cells were still present in the tissue. Omitting or shortening this step resulted in inefficient decellularization of muscle segments thicker than 1 mm (FIG. 1c). Notably, segments less than 1.5 mm thick were harder to slice, exhibited inferior mechanical properties and were less convenient to work with. During the incubation with the detergent solution (0.1-2% Triton® X-100 and 0.05-1.0% ammonium hydroxide in an isotonic solution of 0.9% NaCl), tissue segments became slimy-spongy, lost their solid color and became translucent white (FIG. 1d). When soaked in liquid, the decellular segment generally retained the original visual shape and size of the tissue segment prior to the process (FIGS. 1d-f). Remarkably, after the decellularization process the vascular structures under the pericardia membrane remained visually intact (FIG. 1d). In addition, after the decellularization process the three-dimensional structure of the myocardium tissue is preserved (see for example, the inner wall of the right atrium shown in FIG. 1e). After lyophilization (and before or after cold-gas sterilization), the dry foam-like material was very easy to work with, and readily cut to the desired scaffold size and shape. A custom-made puncher can be used to cut scaffolds to desired size and shape, as well as increase the manufacturing throughput. The dry scaffolds were easily re-hydrated at room temperature in buffered saline or culture medium.

Decellularized matrices are devoid of cells and cell nuclei—Initial verification of decellularization was performed by Hematoxylin and Eosin (H&E) staining of paraffin or frozen sections prepared from the decellularized matrices. Matrices derived from up to 4 mm thick fresh myocardium tissue, with or without epicardial membrane, were frozen and 5 µm thick sections were subjected to H&E staining. As shown in FIG. 2, no cell nucleus could be visible in the matrix, reflecting the acelullarization of the myocardium tissue.

To further confirm that the matrices were indeed devoid of cell nuclei, processed matrices were stained with DAPI. In all matrices prepared from up to 4 mm thick fresh muscle tissue, no nuclei could be found (FIGS. 3a-b). Partially processed matrices exhibited incomplete removal of cell nuclei (FIG. 3c-d). Phenol extraction verified the absence of nucleic acids in the completely treated decellular matrices which were derived from up to 4 mm thick tissues (data not shown).

Decellularized matrices are devoid of cell membranes— Matrices were stained with the DiO stain for detection of residual cell membranes. Matrices, which were partially processed, e.g., that were treated with 0.05 trypsin for only 12 hours and were subjected to only two cycles of 48 hours each in the detergent solution, exhibited some membrane structures as shown in FIGS. 4a-b. However, no cell membranes were detected in any of the decellular matrices which were subjected to the complete decellularization treatment protocol described under Materials and Experimental Methods hereinabove (FIGS. 4c-d).

Optimization of trypsin concentration and incubation time—The concentration of trypsin and the number of washes in trypsin (one or two cycles of 24 hours each) were optimized for complete decellularization on one hand and preservation of the ECM mechanical properties on the other hand. The present inventors have uncovered, through laborious experimentations that one cycle 24 hours in a solution of 0.25% trypsin resulted in a decellularized matrix with poorer mechanical properties as compared to two cycles of 24 hours each in a solution of 0.05% trypsin. In addition, one cycle of 24 hours in a solution of 0.1% trypsin resulted in a decellularized matrix with similar mechanical properties as two cycles of 24 hours each in a solution of 0.05%, but incomplete decellularization.

Optimization of removal of cellular components with the detergent solution—The present inventors have found that the number of wash cycles (for 48 hours each) in the detergent solution [Triton® X-100 (0.1-2%) and ammonium hydroxide (0.05-1.0%) in an isotonic solution of 0.9% NaCl] resulted in no effect on the mechanical properties of the matrix but affected the decellularization process, depending on tissue thickness. For tissue segments of 2-4 mm thick it was found that 2-4 cycles of 48 hours each in the detergent solution are optimal. For tissue segments less than 2 mm thick, 2 cycles of 48 hours each in the detergent solution are sufficient.

Altogether, these findings demonstrate that the decellularization protocol devised by the present inventors resulted in the complete removal of cells, cell nuclei and cell membranes from fresh tissues (e.g., myocardium tissue as exemplified herein), even when using tissue segments as thick as 4 mm.

Example 2

Assessment of Acellularized Matrix Components and Mechanical Properties

To assess the suitability of the myocardium-derived decellularized matrix of the present invention as a scaffold for tissue regeneration, the present inventors have quantified the amount of collagen, elastin and glycosaminoglycans (GAGs) in the matrices and evaluated the structural and mechanical properties of the decellular matrices, as follows.

Materials and Experimental Methods

Collagen quantification—The content of collagen in the decellularized matrix was quantified using the hydroxyprolin assay with slight modifications (Neuman, R. & Logan, M., 1950). Briefly, matrix was hydrolyzed (7N HCl, 105° C., 16-20 hours), diluted and brought to pH=6. Free hydroxyprolin (Fluka, Switzerland) is oxidized to a pyrrole by chloramine T (in Acetate-Citrate buffer pH=6) and the reaction is followed by the pink color resultant of the pyrrole intermediate when reacted with 4-dimethylaminobenzaldehyde (in perchloric acid and iso-propanol) (15 minutes, 58° C.). After cooling, samples' absorbance was spectrometrically measured at 558 nm, and compared to standard hydroxyprolin (Fluka) and collagen type I (Sigma) curves, prepared along with the sample.

Elastin quantification—Elastin was quantified by digestion of the ECM in 0.1 N NaOH and the direct weighing of non-solubilized elastin deposit. Elastin is not a native component of the myocardium itself, however it is present in the blood vessels that vascularize the heart. Loss of elastin serves in this case as an additional parameter for the effect of the decellularization process on the composition of ECM of the resulting matrix.

Glycosaminoglycans quantification—Glycosaminoglycans (GAGs) were quantified using a modification of the colorimetric safranin O assay (Carrino D A et al, 1991). Briefly, samples were digested for 20 hours at 60° C. by papain (60 units per sample; Sigma) and proteinase K (Roche Diagnostics, 250 μg per sample). After centrifugation (3000 g for 10 minutes), supernatants were concentrated by sedimentation in ethanol (80%, 2-4 hours at −20° C.) and centrifugation (3500 g, 1 hour at 4° C.). Pellets were suspended in PBS and added to 10 volumes of safranin O solution (0.02% safranin O [Sigma], 50 mM sodium acetate, pH=4.8), left for one hour and centrifuged. The GAG-safranin O complex in the pellet was solubilized in 1 ml of de-complexation buffer (4 M guanidine-HCL, 10% iso-propanol, 50 mM sodium acetate, pH=6). Absorbance was measured spectrometrically at 536 nm. A standard curve was prepared from ascending concentrations of chondroitin-6-sulfate which were treated the same as the samples.

Assessments of decellular matrix structure—The fibrilar alignment and structure of decellular matrices were examined histochemically, using Masson's trichrome staining, and compared to that of native cardiac tissue. Fresh cardiac tissue and myocardium-derived decellularized matrix were fixed in 4% paraformaldehyde, paraffin blocked, sectioned (5 μm thick) and stained. Hematoxylin stains nuclei in dark blueblack; Biebrich scarlet reagent stains muscle cytoplasm in red; and Aniline blue reagent stains collagen in blue. In addition, structure of the collageneous network was assessed by scanning electron microscopy (SEM), with a JSM-5400 (JEOL, Japan). Decellularized matrix was fixed in 2.5% glutaraldehyde (in PBS), gradually dehydrated in ascending ethanol concentrations (30-99%), air dried and spattered with gold.

SEM and QuantomiX™ WET-SEM—were performed according to standard methods: samples for SEM analysis were fixed for 1 hour in 2.5% glutaraldehyde in PBS, washed three times, 10 minutes each in PBS and once in water, dehydrated in ascending ethanol concentrations, air dried and spattered with gold. Images were captured with a JSM-5400 (JEOL, Japan). For WET-SEM analysis non-fixed samples were stained with Uranyl Acetate and images were captured by QuantomiX™ LTD (QuantomiX Ltd, IL).

Mechanical properties of the decellularized matrix—Tensile strength of the decellularized matrices was measured uni-axially using a rheological measurement instrument (TA500, Lloyd Instruments) equipped with a 10 Newton (N) load cell and a custom-made clamping apparatus. Matrices were first positioned by the clamps at "rest point" (0 stress, 0 strain) and pre-conditioned by ten cycles of strain—release (cyclic strain), where maximum strain was 15% and strain/ un-strain (displacement, relative to initial length) rate was 0.05 mm per second and a cyclic stress—strain curve was plotted. After 2 minutes resting at rest point the matrices were stretched rapidly (0.5 mm per second) to 20% strain and held at that displacement for ten minutes, allowing strain relaxation, and a stress—relaxation time curve was plotted. After 10 minutes resting at rest point the matrices were stretched at constant strain rate of 0.05 mm per second until complete tearing (assigned as 40% stress decrease), and a stress—strain curve was plotted (strain to break). Peak of stress—strain curve indicates relative tensile strength of the matrix, while curve slope indicates matrix resistance (inverse of elasticity).

Experimental Results

Decellularized matrices preserve the majority of the collagen and elastin contents of the original tissue—Quantification of collagen (by the hydroxyproline assay) or of elastin (by direct weighing of the solid elastin deposit) were performed in lyophilized fresh or decellularized myocardium tissues and revealed that about 90% of the collagen and 80% of the elastin present in the fresh myocardium tissue were preserved following the complete decellularization process (FIGS. 5a-b). These results demonstrate that the decellularization protocol devised by the present inventors enables the preservation of most of the collagen and elastin constituents of the ECM present in the original fresh tissues.

Decellularized matrices exhibit high gag quantities—Quantification of Glycosaminoglycan (GAG) was performed according to the modified safranin O assay and revealed that the myocardium-derived decellularized matrices of the present invention exhibit higher GAG content as compared to the commercially available bovine type I collagen matrix (FIG. 7).

Decellularized matrices exhibit high porous and fibrous structures—SEM imaging of the matrices was used to analyze the porous and fibrous structure of the decellularized matrices of the present invention. As shown in FIGS. 6a-c, the myocardium-derived decellularized matrices of the present invention were highly fibrous, with collagen fibers in various thickness and crosslinking levels, and exhibited high porosity.

Decellularized matrices are flexible, yet retain the strength of the original tissue ECM—Mechanical assays revealed that the decellular matrices of the present invention are very elastic yet retain their strength, as demonstrated by returning to similar stress values at repetitive 15% straining (FIG. 8a), minimal decrease of stress at constant 20% strain (FIG. 8b), and withstanding up to 0.42 MPa when strained to 40% (FIG. 8c).

Altogether, these finding demonstrate that the decellularized matrices of the present invention preserve the majority of collagen and elastin contents present in the original fresh myocardium tissue, contain higher GAG quantities as compared to other commercial ECM components (e.g., the commercial collagen type I), are highly fibrous and porous, maintain the mechanical properties of the tissue ECM such as withstanding up to 0.42 MPa when strained to 40%.

Example 3

The Myocardium-Derived Decellularized Matrices are Suitable Scaffolds for Tissue Regeneration To evaluate the suitability of the myocardium-derived decellular matrices as scaffolds for cardiac tissue engineering, the decellular matrices were tested for their ability to support the attachment, morphology and long-term viability of different types of cells including cardiac muscle, fibroblast and endothelial cells, as follows.

Materials and Experimental Methods

Isolation of cardiac fibroblasts—Cardiac fibroblasts were isolated from an adult sheep heart. Briefly, heart tissue was diced to ~1 mm$^3$ segments that were washed in sterile PBS and placed in culture plates without medium. After 10-12 minutes the medium was slowly added to the plates (DMEM with 10% FCS, Gibco) and the tissue segments were incubated untouched for one week (37° C., 5% $CO_2$, humidified atmosphere) before first passage. These primary cardiac fibroblasts were split 1/8 with 0.05% Trypsin-0.02% EDTA, and were not used for more then five passages.

Isolation of cardiac myocytes—Cardiac myocytes were isolated from neonatal 1-2 days old Sprague-Dawley rats. Hearts were washed in PBS-G (0.1% glucose and Penicillin/Streptomycin in PBS) and diced. Following gentle agitation for 12 hours in 0.05% trypsin-0.02% EDTA in HBSS, cardiac cells were dissociated by gentle agitation for 10 minutes at 37° C. in 200 units/mL collagenase type 2 (Worthington) in PBS-G. Cell suspension was collected and added to two volumes of medium. This step was repeated until complete dissociation of the diced hearts. Cell suspension was centrifuged for 5 minutes at 1000 rpm, suspended in DMEM with 10% FCS, run through a 100 μm-pore sieve to remove clusters and pre-plated for one hour in culture dishes in an incubator, to allow adherence of fibroblasts. Non-attached myocyte-enriched cell suspension was collected, centrifuged as before and re-suspended in F-10 nutrient mixture (Life Industries, Ill.) supplemented with 5% fetal calf serum (FCS), 5% donor horse serum (DHS), 1 mM $CaCl_2$ and Penicillin/Streptomycin. Proliferation of any remaining fibroblasts was inhibited by addition of 25 μg/ml bromo-deoxy uridine (BrdU, Sigma) to the culture medium during the first three days of culture.

Seeding of cells on the decellularized matrices of the present invention—Cells were seeded onto the decellularized matrices of the present invention by slowly pipetting cell suspension onto static scaffolds, at a cell concentration of $10^4$ cell per cm$^2$ matrix. Myocytes were seeded and cultured in F-10 nutrient mixture (Life Industries, Ill.) supplemented with 5% FCS, 5% DHS, 1 mM $CaCl_2$ and Penicillin/Streptomycin, and fibroblasts were seeded and cultured in DMEM (Life Industries, Ill.) supplemented with 10% FCS and Penicillin/Streptomycin.

Evaluation of cell adherence and distribution on the decellularized matrices—The extent of cardiac myocyte or fibroblast cell adherence was studied by washing the seeded decellularized matrices with gentle agitation in the culture medium (as described above) and moving the matrices to new culture dishes with fresh medium. Fibroblast-seeded matrices were washed three hours after seeding and myocytes-seeded matrices were washed 24 hours after. At ascending time points after seeding (e.g., 2, 7, 13, 21 and 27 days post seeding), samples of seeded matrices were fixed and stained and the attached cells were counted. Distribution of cells within seeded scaffolds was examined by H&E histochemical staining of frozen sections or paraffin block sections.

DiO staining (Molecular Probes)—was performed according to manufacturer's instructions. Cells were stained for 2 hours prior to seeding and the fluorescence generated by the DiO stain was followed using a fluorescent microscope (488/514 nm). Being non-toxic and photo-stable, DiO staining enables a simple semi-3D tracking of cell distribution and morphology on and within each scaffold for as long as 4 weeks without having to "sacrifice" samples for analyses.

The alamarBlue® assay (Serotec) was performed according to manufacturer's instructions. Being non-toxic, this assay enables to follow cell viability over a period of time for each sample, decreasing measurement variability due to sampling different scaffolds, thus increasing reliability of the assay.

Immunostaining—To evaluate the formation of tissue-like structures, cardiomyocytes were immunostained as follows: anti-Connexin43 was used for gap junctions staining, anti-cardiac Troponin I was used as specific cardiomyocyte marker, and anti-alpha actinin was used for cytoskeletal staining (all primary antibodies from Chemicon, 1:250, overnight at 4° C.). Cy3-conjugated secondary antigen (Jackson, 1:500, 1 hour at RT) was used for fluorescent staining. In addition, cytoskeletal actin was stained for two hours with phalloidin-FITC (Sigma, 0.5 μg/ml in PBS), followed by three washes of 10 minutes each in PBS.

SEM and ET-SEM—were performed as described in Example 1, hereinabove.

Experimental Results

Cardiac fibroblasts adhere to the decellularized matrices of the present invention—The adhesion of cells to the scaffolds was tested by slowly pipetting cell suspension of $10^4$ cardiac fibroblast and myocytes cells per 1 cm$^2$ scaffold surface in 24-well culture plate. The matrices were agitated gently to release dead and non-adhered cells, moved to new wells with fresh medium and further incubated. This procedure was performed three hours after seeding fibroblasts and 24 hours after seeding myocytes. Cells which remained in the original wells, where the matrices were seeded, were collected and counted microscopically by trypan blue exclusion on a haemacytometer. The number of these cells was subtracted from the number of seeded cell to calculate the number of adhered cells. 94.2% of the seeded cardiac fibroblasts remained adhered to the matrices after three hours (ranging 91-97%, SD=1.82, n=12) and 89% of the seeded cardiac myocytes remained adhered to the matrices 24 hours after seeding (ranging 78-93%, SD=5.08, n=10) (data not shown).

The decellularized matrices of the present invention can be remodeled by the seeded cells—As is shown by the DiO staining, the seeded scaffolds began to shrink after approximately two weeks in culture, demonstrating the remodeling ability of the decellularized matrix by the seeded cells (FIGS. 10a-e). By three to four weeks some of the scaffolds were contracted by the fibroblasts and became 1-2 mm spheres, as demonstrated by SEM analysis (FIGS. 9a-d). Evidently, the seeded fibroblasts deposited new collagen fibers to their proximity, as demonstrated by QuantomiX™ WET-SEM™ analysis (FIG. 9e-g).

The decellularized matrices of the present invention are well populated with cells—H&E staining of paraffin or frozen sections showed that at two and three weeks post seeding the scaffolds were well-populated with cells, and that cells were evenly distributed within the scaffolds (FIG. 11a-d).

The cells populated on the decellularized matrices of the present invention are viable—Viability of cells seeded on the scaffolds was quantitated using the alamarBlue® assay. After seeding medium was changed every 2-3 days. Every second medium change scaffolds were gently moved to new wells to prevent artifact results caused by the outgrowth of fibroblasts from the matrix onto the culture dish. The density and distribution of the cardiac fibroblasts in the scaffolds was shown by the DiO staining (FIGS. 10a-e) and the histochemical H&E staining (FIGS. 11a-d). The viability of cells on each scaffold, which was measured two days after seeding, was denoted 100%. Further measurements for each scaffold were related to it's own initial viability value. As is shown in FIGS. 12a-b, both cardiac fibroblasts and cardiomyocytes were highly viable (80% or more) for the first three weeks post seeding. In addition, at four weeks post seeding, ~77% and ~68% of the cardiac fibroblasts or the cardiomyocytes, respectively, remained viable.

The decellularized matrices of the present invention support the spontaneous concert pulsatile beating of cardiomyocytes which are seeded thereon—Neonatal rat cardiomyocytes were seeded at $10^4$ cells per 1 cm$^2$ on various sizes of scaffolds, including 1 cm$^2$ (in 24-well plates), ~2 cm$^2$ (in 12-well plates), 5-6 cm$^2$ (in 6-well plates), and even as large as ~12 cm$^2$ (~5×2.5 cm in 6-cm plates). During culturing period the culture medium (F-10 with 10% FCS, 1 mM $CaCl_2$, antibiotics) was replaced every 2-3 days. BrdU was added during the first 3 days to prevent proliferation of fibroblasts. Scaffolds of all sized began to show spontaneous beating as shortly as 1-2 days post seeding. By 3-4 days post seeding most matrices exhibited spontaneous concert pulsatile beating, clearly visible by the naked eye, some rather vigorous. Some of the matrices continued to beat as long as three weeks. Such long-term concert pulsatile beating indicates the formation of mature functioning electrophysiological cardiac tissue phenotype.

Altogether, these findings demonstrate that the decellularized matrices of the present invention are capable of supporting the adherence, growth and viability of cells (e.g., fibroblasts or cardiomyocytes), are capable of being remodeled by the cells seeded thereon and are capable of spontaneous concert pulsatile beating when seeded with cardiomyocytes.

Example 4

Artery-Derived Decellularized Matrices

Decellularized matrices prepared from an artery tissue according to the teachings of the present invention were evaluated for their complete decellularization, structural and mechanical characteristics and non-immunogenic properties using histological analysis, DNA analysis, scanning electron microscopy (SEM), collagen measurements and RT-PCR analysis and stress-strain analyses, as follows.

Materials and Experimental Methods

Preparation of artery-derived decellularized matrices—Porcine blood vessels were obtained aseptically from terminated animals. The blood vessels from the descending aorta to the bifurcation (branching) of the femoral arteries were harvested. Upon harvesting, blood vessels with a diameter ranging from 5 mm to 10 mm were cut into segments of 5-6 cm in length and were subjected to the decellularization method essentially as described in Example 1, hereinabove. Specifically, arteries were incubated in 0.05% trypsin solution (containing 0.02% EDTA) for two consecutive incubation periods of 24 hours each at 37° C. (using fresh trypsin solution for each incubation period). The detergent used for the decellularization processes was 1% Triton X-100 with 1% ammonium hydroxide. The arteries were incubated in the detergent solution for three consecutive incubation periods of 72 hours each, at 4° C. (using fresh detergent solution for each incubation period). Scaffolds were then washed three times, 24 hours each, with saline to remove traces of cell debris and agents. Scaffolds were washed for 48 hours with double distilled water (DDW), lyophilized and sterilized using cold gas (ethylene oxide).

Assessment of decellularized matrices—was performed as described under "Materials and Experimental Methods" of Examples 1 and 2 of the Examples section which follows.

Culture media for cells seeded on artery-derived matrices—Smooth muscle cells (SMCs) were cultured on DMEM low glucose medium (Gibco USA) supplemented with 10% fetal calf serum (FCS) and Penicillin/Streptomycin (at a concentration of 250 units/ml). Human umbilical cord vascular endothelial cells (HUVEC) or bovine corneal endothelial cells (BCEC) were cultured on M199 medium (Gibco USA) supplemented with 20% FCS, Penicillin/Streptomycin (at a concentration of 250 units/ml) and 5 ng/ml bFGF.

Seeding techniques—SMC were seeded on the outer side of the decellularized arteries and HUVEC or BCEC on the inner side of the decellularized arteries. Seeding techniques included the static or the centrifugal (i.e., dynamic) seeding methods, as follows.

Static seeding—For the static seeding, cells were trypsinized, centrifuged and resuspended in 50 µL of fresh medium. Sterilized scaffolds were ventilated for a few days and soaked overnight in sterile fresh medium (according to cell type) before seeding. The scaffolds were cut into pieces of 1 cm×1 cm. Cell suspension was carefully pipetted onto the scaffold: SMC on the outer side of the scaffold and HUVEC or BCEC on the inner side. The cells were allowed to attach to the scaffolds for 20 minutes, following which the scaffolds were immersed in medium and placed in an incubator of 37° C. with 5% $CO_2$.

Centrifugal (or dynamic) seeding—For the dynamic seeding, SMC were trypsinized, centrifuged and resuspended in 5 ml of fresh DMEM low glucose medium. Patches of scaffolds were placed, lumen side down, in a tube filled with agarose. The agarose served as a substrate for nailing the scaffolds, using sterile syringe needles. The cell suspension was pipetted onto the scaffold and the scaffolds were subjected to 10 rounds of centrifugation, 1 minute each, at 2500 rpm. Scaffolds were then placed in tissue culture dishes, immersed in medium and placed in an incubator of 37° C. with 5% $CO_2$.

Culturing techniques—Seeded matrices were cultured over time using the static or the dynamic approaches, as follows.

Static culturing—For the static culture, scaffolds were immersed in the relevant medium and placed in an incubator. Medium was changed every other day.

Dynamic culturing—For the dynamic culture, scaffolds were placed in a 100 ml spinner flask (Bellco Glass). Culture medium (50 ml) was added to the seeded scaffold and culturing was effected by subjecting the spinner flasks to stirring of 40 rpm for 7 weeks in an incubator. Medium was changed every 3 days.

In all cases, SMC were allowed to grow for 4 weeks. Seeded scaffolds were then fixed, processed and subjected to histological analysis.

Immunostaining analysis—was performed using the α-smooth muscle actin antibody (Sigma, A2547, dilution 1:500), procollagen I (Chemicon, MAB 1913, dilution 1:100).

Coating scaffolds—For HUVEC adhesion and viability studies, plates/scaffolds were coated with four different coatings: PBS (control), 0.2% gelatin (Sigma), 5 µg/ml fibronectin (Biological industries, IL) or corneal matrix (CM). For CM coating, BCEC were allowed to grow until confluency, following which the scaffolds were treated with 0.5% Triton X-100 and 50 mM ammonium hydroxide in PBS. After a few minutes of treatment, the cells were detached from the surface, leaving an intact ECM. This ECM was washed with PBS and then stored at 4° C. in PBS supplemented with 1% Penicillin/Streptomycin and 0.4% fungizone (Gibco, USA). All other solutions were used to coat the plates/scaffolds on the day of the experiment and were left on the plate for 2 hours in an incubator prior to use.

Immunogenicity and host response—To study host immunogenic response to the decellularized matrix, 0.5 cm×0.8 cm pieces of decellularized matrices were implanted subcutaneously in 4-5 weeks old C57 Black male mice. Sham mice in which an incision was made but no polymer (i.e., the decellularized matrix) was implanted were also included in the study. Mice were divided randomly into 2 groups according to the evaluated time points: 1 week and 2 weeks post-surgery. Each group consisted of 5 experimental mice and 3 sham mice. At the end of each time point, the mice were sacrificed and their lymph nodes, implanted scaffolds and surrounding skin were harvested. In the control sham group the site of incision was taken. Due to technical reasons the scaffolds and the surrounding skin harvested after 1 week were paraffin-embedded, while the scaffold and surrounding skin harvested after 2 weeks were frozen. All samples were sliced and subjected to histological (H&E) and immunohistological [macrophage staining using anti-F4/80 antigen (# MCA497R), dilution 1:100; Serotec (Raleigh, N.C.)] evaluations by a well-experienced pathologist.

RT-PCR analysis of TNF-α and IL-1β from lymph nodes of implanted mice—To further evaluate the immunogenicity of the decellularized matrices of the present invention, samples of both lymph nodes (i.e., from the treated side and the untreated side of the animal) were dissected and RNA was extracted using the Tri-reagent (Sigma) with a pellet pestle. The extracted RNA was reverse-transcribed and amplified with the following PCR primers: for TNF-α transcripts—TNF-α Fw: 5'-GAT TTG CTA TCT CAT ACC AGG AGA A (SEQ ID NO:7) and TNF-α Rev: 5'-GAC AAT AAA GGG GTC AGA GTA AAG G (SEQ ID NO:8); for IL-1β transcripts—IL-1β Fw: 5'-CAT GGA ATC TGT GTC TTC CTA AAG T (SEQ ID NO:9) and IL-1β Rev: 5'-GTT CTA GAG AGT GCT GCC TAA TGT C (SEQ ID NO:10); for mouse GAPDH transcripts—GAPDH Fw: 5'-ACC CAG AAG ACT GTG GAT GG (SEQ ID NO:11) and GAPDH Rev: 5'-CTT GCT CAG TGT CCT TGC TG (SEQ ID NO:12). Products were electrphoressed on 2% agarose gels and quantified using the ImageJ software (NIH, USA).

Evaluation of the formation of new ECM components (e.g., elastin and procollagen III) following seeding with SMCs—RNA samples of SMCs that were seeded on scaffolds were subjected to DNAse treatment and then reverse-transcribed using Reverse-iT™ 1$^{st}$ strand synthesis kit (Abgene, Surrey, UK). cDNA was amplified in a thermal cycler (PTC-200, MJ Research) after adding ReddyMix™ PCR master mix. PCR primers for elastin were: Elastin Fw: 5'-CCT TGG AGG TGT GTC TCC AG (SEQ ID NO:1), Elastin Rev: 5'-ACT TTC TCT TCC GGC CAC AG (SEQ ID NO:2); PCR primers for procollagen III were: procollagen III Fw: 5'-GCA GGG AAC AAC TTG ATG GT (SEQ ID NO:3), procollagen III Rev: 5'-CGG ATC CTG AGT CAC AGA CA (SEQ ID NO:4); Standardization was conducted with sheep GAPDH using the following PCR primers: GAPDH Fw: 5'-AGG TCG GAG TCA ACG GAT TT (SEQ ID NO:5), GAPDH Rev: 5'-CCT TCT CCA TGG TAG TGA AGA CC (SEQ ID NO:6). Products were electrphoressed on 2% agarose gels. Quantification of bands' intensity was accomplished by using ImageJ software (NIH, USA).

Assessment of mechanical properties of the decellularized scaffolds—was performed as described in Example 2, hereinabove.

Experimental Results

Artery-derived decellularized matrices are devoid of cellular components and maintain the collagen and elastin content and structure of the native artery—Artery-derived decellularized matrices were prepared as described under "Materials and Experimental Methods" hereinabove. FIGS. 13a-b demonstrate a porcine artery before (FIG. 13a) and after (FIG. 13b) the decellularization process. Histological evaluation of the decellularized artery-derived matrix revealed the absence of cell nuclei and the preservation of the collagen and elastin structure following decellularization (FIGS. 14a-b). In addition, quantification of the elastin and collagen contents in decellularized matrices demonstrated that decellularized matrices from various sections of the arteries (e.g., the proximal, center of distal sections) maintain similar quantities of collagen (about 30-35% of the dry artery weight) or elastin (about 15-20% of the dry artery weight). Moreover, SEM analysis revealed the absence of cell nuclei from both the outer and the luminal sides of the processed decellularized artery-derived matrices (FIGS. 16a-d).

Artery-derived decellularized matrices are devoid of nucleic acids—Traces of porcine DNA in the arteries following the decellularization process may evoke an immune response when implanted to other species. To determine whether the decellularized artery-derived matrices of the present invention are devoid of DNA, genomic DNA was extracted from the native or the decellularized arteries and DNA samples were subjected to agarose gel electrophoresis. As is shown in FIG. 17, no traces of genomic DNA were detected following decellularization.

Artery-derived decellularized matrices are suitable scaffolds for cell proliferation in vitro—Decellularized matrices were pre-coated with fibronectin (5 µg/ml, 2 hours in a 37° C. incubator), following which smooth muscle cells (SMCs) were seeded on one side of the matrix at a seeding density of $5-20 \times 10^6$ cells (FIGS. 18a-c). It will be appreciated that in order to obtain an engineered tissue such as a vessel, endothelial cells are seeded on the counterlateral side of the decellularized matrices after obtaining a confluent layer of smooth muscle cells. Further histological and immunocytochemical evaluations performed using markers for smooth muscle cells such as anti-alpha smooth muscle actin (FIGS. 19e and f), which labels smooth muscle actin, demonstrates a successful seeding of SMCs on the collagen artery-derived decellularized matrices. One week after seeding, the scaffolds were confluent with endothelial cells, but the cells were disoriented (data not shown). Four weeks after seeding the decellularized scaffolds with endothelial and SMCs, a layer of endothelial cells had developed as seen in FIGS. 19a and c. The SMC seeded on the outer perimeter of the vessel remained attached to the scaffold for a period of three months in culture (FIGS. 19e and f). The Masson staining revealed a limited SMC cell migration into the vessel wall but the pale red color indicates the development of neo muscular tissue derived from the SMC seeded scaffolds.

Centrifugal seeding and dynamic culturing results in efficient penetration of SMCs to the scaffolds—To determine the optimal conditions for SMC and endothelial seeding and growth on the decellularized scaffolds, several seeding and culture techniques were utilized. These include static seeding followed by static culturing, centrifugal seeding followed by static culturing and centrifugal seeding followed by dynamic culturing. The efficiency of the various seeding and culturing techniques was evaluated using histological (e.g., H&E staining) and immunohistochemical (e.g., using α-smooth muscle actin immunostaining) analyses. As is shown in FIGS. 20a-f, centrifugal seeding resulted with better penetration of SMCs into the scaffolds than a static seeding, whereas a dynamic environment resulted in even greater penetration and alignment of the cells along the elastin fibers.

Centrifugal seeding and dynamic culturing results in efficient remodeling of the decellularized scaffolds with new collagen deposits—Secretion of collagen and elastin by the seeded cells is an important process, which leads to the biochemical and mechanical remodeling of the scaffold into an artery. Therefore, Masson's staining was used to detect the collagen and elastin secreted by the SMC after seeding and culturing on the scaffolds. The secretion of collagen was detected by immunostaining of the newly produced collagen type I, as expressed by its precursor, procollagen I. As is shown in FIGS. 21a-c the vast amount of new collagen secreted by the SMC cells was deposited in scaffolds seeded using a centrifugal method and cultured using a dynamic method. To further examine whether other ECM components are produced following seeding with SMCs, the level of elastin, collagen type III and GAPDH mRNA was detected by RT-PCR analysis. As is shown in FIGS. 22a-c, the level of elastin mRNA was 2.3 times higher in scaffolds seeded with cells using the centrifugal method and static culturing as compared with scaffolds seeded and cultured using the static methods. In addition, the level of elastin mRNA in scaffolds subjected to dynamic culturing was 4 times higher than that of scaffolds subjected to static culturing method. On the other hand, the levels of collagen III mRNA were similar in scaffolds seeded or cultured using the different approaches.

Centrifugal seeding and dynamic culturing results in efficient proliferation of cells seeded on the decellularized matrices—The proliferation of cells on the decellularized scaffolds was examined using Alamar-Blue reagent. This assay was performed on SMC every week, for 4 weeks, and values were normalized to the number of cells. As is shown in FIG. 24, a significant difference in the number of cells was observed 6 days following seeding the scaffolds using the different seeding methods. However, at day 27-post seeding, the culture conditions became dominant, showing that cells cultured in a dynamic environment proliferate better when compared to cells cultured in a static environment.

In an attempt to further improve the seeding conditions, another dynamic seeding approach was used. SMC were seeded overnight in a spinner flask to allow adhesion of cells to the decellularized scaffolds, followed by culturing in the spinner flask for 7 weeks. As is shown in FIGS. 25a-d, one day after seeding, a uniform coverage of the scaffold by the cells was accomplished (FIG. 25a). At three weeks post-seeding, the cells have proliferated but their penetration capacity was still limited (FIG. 25b). At 7 weeks post-seeding, cells have already aligned circumferentially along the artery wall, covering most of its area (FIGS. 25c and d).

Coating of scaffolds with corneal matrix (CM) results in uniform coverage of HUVEC—The effect of coating scaffolds was determined in scaffolds coated with CM or PBS (i.e., uncoated, bare scaffolds) using histological (H&E) and immunohistochemical staining. FIGS. 23a-d show representative staining of Human Umbilical Cord Vascular Endothelial Cord (HUVEC) following 9 days in culture on PBS or CM coated scaffolds. While seeding of HUVEC on the bare scaffold resulted in their incomplete coverage of the scaffold surface (FIGS. 23a and b), coating of the scaffold with CM resulted in a more uniform coverage of HUVEC (FIGS. 23c and d).

The Decellularized Matrices of the Present Invention are Non-Immunogenic when Implanted in a Subject To eliminate any possible complications when using scaffolds as vascular grafts in vivo, the immune reaction against the decellularized scaffolds was tested in C57 black mice following implantation of patches of 0.5 cm×0.8 cm. The implanted patches were harvested at different time points (one and two weeks post-implantation) and the immune response was examined by histological analysis of inflammatory or immune cells and by RT-PCR analysis of proinflammatory factors (TNF-α and IL-1β) of RNA extracted from the lymph nodes of the implanted animals. One and two weeks post surgery the surrounding tissues of the sham mice (not shown) presented similar results to those observed in animals implanted with the polymers (i.e., the decellularized matrices of the present invention) (FIGS. 26a-d). These included several granulocytes and elongated fibroblasts (typical for a wound healing response). Furthermore, RT-PCR analysis of the proinflammatory factors TNF-α and IL-1β revealed no increase in the proinflammatory factors between one to two weeks and was similar in the sham-operated mice (data not shown).

The Artery-Derived Decellularized Matrices Maintain the Mechanical Properties of the Artery ECM The mechanical properties of the artery-derived decellularized scaffolds of the present invention were tested using the strain-stress and/or load-elongation methods described in Example 2 hereinabove and in Fung, Y. C. Biomechanics: Mechanical properties of living tissues, $2^{nd}$ Edn. Springer-Verlag, NY (1993), and were compared to those of native artery tissues or decellularized scaffolds following seeding with cells. Briefly, decellularized artery-derived matrices were seeded with SMCs using the centrifugal seeding method followed by dynamic culturing in spinner flasks for 2 weeks. Scaffolds (seeded or un-seeded decellularized matrices or native artery tissues) were subjected to stress-strain (elongation) analyses which included straining the scaffolds uniaxially until break while recording the scaffold's circumferential stress. As is shown in Table 1 hereinbelow, following decellularization, the scaffolds exhibited a slight decrease in elasticity, as evident in a change of the ultimate stress from 2.3±0.08 MPa in native arteries to 2.24±0.15 MPa in decellularized scaffolds, and an increase in the stiffness, as evident in a change of the ultimate strain from 145.9±8.8% in native arteries to 108.5±14.5% in decellularized scaffolds and by the change in Young's modulus value from 2.7±0.7 MPa in native arteries to 4.8±1.8 MPa in decellularized scaffolds. However, following seeding the decellularized scaffolds with SMC (e.g., using the centrifugal seeding and dynamic culturing for two weeks) the matrices regained the mechanical properties of the native artery tissues as evident by elasticity of 3.02±0.37 MPa, ultimate strain of 145.3±17.8% and Young's modulus value of 4±1 MPa.

TABLE 1

Mechanical properties of native, unseeded or seeded decellularized matrices

|  | Native arteries | Decellularized artery-derived matrices | SMCs-seeded decellularized artery-derived matrices |
|---|---|---|---|
| Ultimate Stress (MPa) | 2.3 ± 0.08 | 2.24 ± 0.15 | 3.02 ± 0.37 |
| Ultimate Strain (%) | 145.9 ± 8.8 | 108.5 ± 14.5 | 145.3 ± 17.8 |
| Young's Modulus (MPa) | 2.7 ± 0.7 | 4.8 ± 1.8 | 4 ± 1 |

Table 1: Presented are the ultimate stress (measured in MPa), ultimate strain (measured in percentages with respect to the strain at the rest point) and Young's modulus values (presented in MPa) according to the strain-stress curves. Results represent average ± SD as measured for at least 8 samples in each case.

Altogether, these results demonstrate that artery-derived decellularized matrices prepared according to the teachings of the present invention are completely devoid of cellular component, are suitable scaffolds for cells in terms of cell adherence, population, proliferation, viability and mechanical properties, are remodeled upon seeding with cells and are non-immunogenic when implanted in a subject. In addition, these results demonstrate the superiority of the centrifugal seeding and dynamic culturing methods over the static seeding and culturing methods of cells on the scaffolds of the present invention.

Analysis and Discussion

The results presented in Examples 1-4 hereinabove demonstrate, for the first time, a method of generating a completely decellularized matrix from a natural tissue (e.g., a myocardium or an artery) which is non-immunogenic and which exhibits structural and mechanical properties of the tissue ECM and thus is suitable for tissue regeneration.

It is well accepted that ECM-based scaffolds are superior to synthetic ones, in terms of their biologic properties, such as cell adherence, proliferation and differentiation. However most scaffolds presented so far were lacking the mechanical strength and/or elasticity required for tissue reconstruction or tissue engineering, and methods for cross-linking were needed. The decellular myocardium matrix of the present invention possesses the advantageous combination of a biological scaffold with mechanical properties required for tissue engineering and tissue reconstruction, and particularly that of the heart.

The decellularization method was optimized for complete removal of cellular components, such as nuclei, remaining DNA of broken nuclei, cellular membranes and proteins. All materials used in the decellularization process are generally recognized as safe ("GRAS") according to the FDA. The process is simple, inexpensive and reproducible. Loss of ECM components during the process was relatively minimal, as evaluated by quantification of collagen and elastin. The glycosaminoglycan content in the decellularized matrix of the present invention is higher compared to the commercially available type I collagen (Sigma) often used in cardiac tissue engineering studies. This fact may prove advantageous, as glycosaminoglycans are important for the normal differentiation and maturation of tissues. The resulting decellularized matrix of the present invention was shown to be non-immunogenic when implanted in a subject.

After lyophilization and sterilization, the dry scaffolds exhibited remarkably long shelf life. The scaffolds of the present invention could be easily cut into the desired shape and size, and are easy to work with after re-hydration. The scaffolds are not sensitive to degradation by hydrolysis, and can be kept in sterile PBS for more than 8 months, without change of collagen content.

Seeding of cells on the scaffolds showed that the scaffolds support long term adherence and viability of the seeded cells, and that the seeded cells readily remodeled the scaffolds in vitro. Cardiomyocytes formed concert spontaneous beating shortly post seeding, indicating that upon seeding with cells the scaffolds support the formation of normal myocardium phenotype (i.e., engineered tissue).

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

REFERENCES

Additional References are Cited in Text

Badylak S F, Park K, Peppas N, McCabe G, Yoder M. Marrow-derived cells populate scaffolds composed of xenogeneic extracellular matrix. Exp Hematol. 2001 November; 29(11):1310-8.

Carrino D A, Arias J L, Caplan A I. A spectrophotometric modification of a sensitive densitometric Safranin O assay for glycosaminoglycans. Biochem Int. 1991 June; 24(3): 485-95.

Cebotari S, Mertsching H, Kallenbach K, Kostin S, Repin O, Batrinac A, Kleczka C, Ciubotaru A, Haverich A. Construction of autologous human heart valves based on an acellular allograft matrix. Circulation. 2002 Sep. 24; 106 (12 Suppl 1):163-168.

Jux C, Wohlsein P, Bruegmann M, Zutz M, Franzbach B, Bertram H. A new biological matrix for septal occlusion. J Interv Cardiol. 2003 April; 16(2):149-52.

Kofidis T, Akhyari P, Wachsmann B, Boublik J, Mueller-Stahl K, Leyh R, Fischer S, Haverich A. A novel bioartificial myocardial tissue and its prospective use in cardiac surgery. Eur J Cardiothorac Surg. 2002 August; 22(2):238-43.

Neuman, R. & Logan, M. (1950) *J. Biol. Chem.* 186, 549-556

Radisic M, Euloth M, Yang L, Langer R, Freed L E, Vunjak-Novakovic G. High-density seeding of myocyte cells for cardiac tissue engineering. Biotechnol Bioeng. 2003 May 20; 82(4):403-14.

Shachar M, Cohen S Heart Fail Rev. Cardiac tissue engineering, ex-vivo: design principles in biomaterials and bioreactors. 2003 July; 8(3):271-6.

Steinhoff G, Stock U, Karim N, Mertsching H, Timke A, Meliss R R, Pethig K, Haverich A, Bader A. Tissue engineering of pulmonary heart valves on allogenic acellular matrix conduits: in vivo restoration of valve tissue. Circulation. 2000 Nov. 7; 102(19 Suppl 3):III50-5.

Vesely I. Heart valve tissue engineering. Circ Res. 2005 Oct. 14; 97(8):743-55.

Zimmermann W H, Eschenhagen T. Cardiac tissue engineering for replacement therapy. Heart Fail Rev. 2003 July; 8(3):259-69.

Zimmermann W H, Didie M, Wasmeier G H, Nixdorff U, Hess A, Melnychenko I, Boy O, Neuhuber W L, Weyand M, Eschenhagen T. Cardiac grafting of engineered heart tissue in syngenic rats. Circulation. 2002 Sep. 24; 106(12 Suppl 1):I151-7.

What is claimed is:

1. A method of generating a decellularized extracellular matrix (ECM) of a myocardium tissue, comprising:
   (a) subjecting the myocardium tissue to a hypertonic buffer to thereby obtain increased intercellular space within the myocardium tissue;
   (b) subjecting the myocardium tissue resultant of step (a) to an enzymatic proteolytic digestion to thereby obtain digested cellular components within the myocardium tissue; and subsequently
   (c) removing said digested cellular components from the myocardium tissue;
   thereby generating the decellularized ECM of the myocardium tissue.

2. The method of claim 1, further comprising:
   (d) subjecting the myocardium tissue resultant of step (a) to a nuclease treatment to thereby obtain nucleic acid—free tissue.

3. The method of claim 2, wherein step (d) is effected following or concomitant with step (b).

4. The method of claim 1, wherein said hypertonic buffer comprises 1-1.2% NaCl.

5. The method of claim 1, wherein said hypertonic buffer comprises 1.1% (w/v) NaCl.

6. The method of claim 1, wherein said enzymatic proteolytic digestion comprises trypsin digestion.

7. The method of claim 6, wherein said trypsin is provided at a concentration selected from the range of 0.05-0.25% (w/v).

8. The method of claim 6, wherein said trypsin is provided at a concentration of 0.05% (w/v).

9. The method of claim 6, wherein said enzymatic proteolytic digestion is effected for about 24 hours.

10. The method of claim 1, wherein step (b) is effected at least twice.

11. The method of claim 1, wherein said removing comprises subjecting the tissue to a detergent solution.

12. The method of claim 11, wherein said detergent solution comprises TRITON-X-100.

13. The method of claim 12, wherein said detergent solution further comprises ammonium hydroxide.

14. The method of claim 12, wherein said Triton-X-100 is provided at a concentration selected from the range of 0.1-2% (v/v).

15. The method of claim 12, wherein said Triton-X-100 is provided at a concentration of 1% (v/v).

16. The method of claim 13, wherein said ammonium hydroxide is provided at a concentration selected from the range of 0.05-1.0% (v/v).

17. The method of claim 13, wherein said ammonium hydroxide is provided at a concentration of 0.1% (v/v).

18. The method of claim 11, wherein said subjecting the tissue to said detergent solution is effected for at least 24-48 hours.

19. The method of claim 11, wherein said subjecting the tissue to said detergent solution is effected for 2-4 times.

20. The method of claim 1, wherein the myocardium tissue comprises myocardium tissue segments.

21. The method of claim 20, wherein each of said myocardium tissue segments is 2-4 mm thick.

22. A scaffold formed by the method of claim 1.

23. A scaffold comprising a myocardium-derived decellularized ECM which is completely devoid of cellular components.

24. The scaffold of claim 23, wherein said cellular components comprise cell nuclei, nucleic acids, residual nucleic acids, cell membranes and/or residual cell membranes.

25. The scaffold of claim 23, wherein said myocardium-derived decellularized ECM maintains mechanical and structural properties of a myocardium tissue ECM.

26. The scaffold of claim 23, wherein said myocardium-derived decellularized ECM is capable of remodeling upon seeding with cells.

27. The scaffold of claim 25, wherein said myocardium-derived decellularized ECM maintains at least 90% of a collagen content and at least 80% of an elastin content of a myocardium tissue.

28. The scaffold of claim 25, wherein said myocardium-derived decellularized ECM is characterized by a stress value of at least 0.4 MPa when strained to 40%.

29. The scaffold of claim 25, wherein said myocardium tissue is a pig myocardium tissue.

30. An engineered tissue comprising the scaffold of claim 22 and a population of at least one cell type seeded and proliferated therein.

31. An engineered tissue comprising the scaffold of claim 23 and a population of at least one cell type seeded and proliferated therein.

32. The engineered tissue of claim 31, wherein said at least one cell type is cardiomyocyte and whereas said myocardium-derived decellularized ECM exhibits spontaneous beating.

33. The engineered tissue of claim 32, wherein said spontaneous beating is in concert.

34. A method of ex vivo forming a tissue, the method comprising:
   (a) seeding the scaffold of claim 22 with at least one type of cells; and
   (b) providing said cells with growth conditions so as to allow said cells to populate in said scaffold;
   thereby ex vivo forming the tissue.

35. A method of ex vivo forming a myocardial tissue, the method comprising:
   (a) seeding the scaffold of claim 23 with at least one type of cells; and
   (b) providing said cells with growth conditions so as to allow said cells to populate in said scaffold;
   thereby ex vivo the forming the myocardial tissue.

36. The method of claim 35, wherein said at least one type of cells comprises cardiomyocytes.

37. The method of claim 35, wherein said at least one type of cells comprises cardiac fibroblasts.

38. A method of in vivo forming of a tissue, the method comprising implanting the scaffold of claim 22 in a subject thereby in vivo forming the tissue.

39. A method of in vivo forming a myocardial tissue, the method comprising implanting the scaffold of claim 23 in a subject thereby in vivo forming the myocardial tissue.

40. The method of claim 1, wherein said cellular components comprise a cell membrane.

41. A method of generating a decellularized extracellular matrix (ECM) of a myocardium tissue, comprising:
   (a) subjecting the myocardium tissue to a hypertonic buffer to thereby obtain increased intercellular space within the myocardium tissue;
   (b) subjecting the myocardium tissue resultant of step (a) to an enzymatic proteolytic digestion to thereby obtain digested cellular components within the myocardium tissue; and subsequently
   (c) subjecting the tissue resultant from step (b) to a detergent solution to thereby remove said digested cellular components from the myocardium tissue;
   thereby generating the decellularized ECM of the myocardium tissue.

42. A scaffold comprising a myocardium-derived decellularized ECM which is completely devoid of cellular components, wherein said cellular components comprise cell membranes and/or residual cell membranes.

43. The scaffold of claim 42, wherein said cellular components comprise further comprise cell nuclei, nucleic acids, and/or residual nucleic acids.

* * * * *